US009981027B2

(12) United States Patent
Sawada et al.

(10) Patent No.: US 9,981,027 B2
(45) Date of Patent: May 29, 2018

(54) VACCINE AGAINST COLIBACILLOSIS

(71) Applicants: IDEMITSU KOSAN CO., LTD., Chiyoda-ku (JP); NATIONAL CENTER FOR GLOBAL HEALTH AND MEDICINE, Shinjuku-ku (JP)

(72) Inventors: Kazutoshi Sawada, Sodegaura (JP); Takeshi Matsui, Sodegaura (JP); Eiji Takita, Sodegaura (JP); Takashi Hamabata, Shinjuku-ku (JP); Toshio Sato, Shinjuku-ku (JP)

(73) Assignees: IDEMITSU KOSAN CO., LTD., Chiyoda-ku (JP); NATIONAL CENTER FOR GLOBAL HEALTH AND MEDICINE, Shinjuku-ku (JP)

( * ) Notice: Subject to any disclaimer, the term of this patent is extended or adjusted under 35 U.S.C. 154(b) by 0 days. days.

(21) Appl. No.: 15/039,697

(22) PCT Filed: Nov. 25, 2014

(86) PCT No.: PCT/JP2014/081114
§ 371 (c)(1),
(2) Date: May 26, 2016

(87) PCT Pub. No.: WO2015/080100
PCT Pub. Date: Jun. 4, 2015

(65) Prior Publication Data
US 2017/0028046 A1 Feb. 2, 2017

(30) Foreign Application Priority Data
Nov. 26, 2013 (JP) ................. 2013-243932

(51) Int. Cl.
*A23K 50/30* (2016.01)
*A61K 39/112* (2006.01)
*C07K 14/245* (2006.01)
*C07K 14/25* (2006.01)
*A61K 39/108* (2006.01)
*A61K 38/16* (2006.01)
*A23K 20/00* (2016.01)
*A61K 39/00* (2006.01)

(52) U.S. Cl.
CPC .......... *A61K 39/0283* (2013.01); *A23K 20/00* (2016.05); *A23K 50/30* (2016.05); *A61K 38/164* (2013.01); *A61K 39/0258* (2013.01); *C07K 14/245* (2013.01); *C07K 14/25* (2013.01); *A61K 2039/542* (2013.01); *A61K 2039/552* (2013.01); *C07K 2319/00* (2013.01)

(58) Field of Classification Search
None
See application file for complete search history.

(56) References Cited

U.S. PATENT DOCUMENTS

2008/0107653 A1* 5/2008 Vermeij ............. A61K 39/0258 424/139.1
2011/0231960 A1* 9/2011 Sawada .................. A61K 39/00 800/298

FOREIGN PATENT DOCUMENTS

| EP | 2 287 300 A1 | 2/2011 |
| JP | 2006-527990 A | 12/2006 |
| JP | 2012-19719 A | 2/2012 |
| WO | 2009/133882 A1 | 11/2009 |

OTHER PUBLICATIONS

Li et al. 2013 (Expression of Recombinant *Escherichia coli* heat-labile enterotoxin B subunit and Shiga Toxin 2 B Subunit Proteins and Evaluation of Humoral Immune Responses Induced in Mice; Chinese Journal of Animal Infectious Disease (5): 13-20).*
Ran et al. 2008 (The immunogenicity of fusion protein linking the carboxyl terminus of the B subunit of Shiga toxin 2 to the B subunit of *E. coli* heat-labile enterotoxin; Veterinary Microbiology 127: 209-215).*
Gomord et al. 2004 (Posttranslational modification of therapeutic proteins in plants; Current Opinion in Plant Biology 7:171-181).*
International Search Report dated Feb. 24, 2015, in PCT/JP2014/081114 Filed Nov. 25, 2014.
Ran, et al., "The immunogenicity of fusion protein linking the carboxyl terminus of the B subunit of Shiga toxin 2 to the B subunit of *E. coli* heat-labile enterotoxin," Veterinary Microbiology, vol. 127, No. 1-2, 2008 pp. 209-215.
Li, et al., "Expression of recombinant *Escherichia coli* heat-labile enterotoxin B subunit and Shiga toxin 2 B subunit proteins and evaluation of humoral immune responses induced in mice," Chinese Journal of Animal Infectious Diseases, vol. 21, No. 5, 2013 pp. 13-20.
Iturriaga et al.-"Endoplasmic Reticulum Targeting and Glycosylation of Hybrid Proteins in Transgenic Tobacco", The Plant Cell, vol. 1, pp. 381-390, Mar. 1989.
Extended European Search Report dated Mar. 24, 2017 in Patent Application No. 14866703.3.
Takeshi Matsui, et al., "Production of double repeated B subunit of Shiga toxin 2e at high levels in transgenic lettuce plants as vaccine material for porcine edema disease", Transgenic Research, XP002634124, Oct. 21, 2010, pp. 1-14.
Tae-Geum Kim, et al., "Synthesis and assembly of *Escherichia coli* heat-labile enterotoxin B subunit in transgenic lettuce (*Lactuca sativa*)", Protein Expression and Purification, XP005727960, vol. 51, No. 1, 2007, pp. 22-27.
International Preliminary Report on Patentability and Written Opinion dated Jun. 9, 2016 in PCT/JP2014/081114 (submitting English translation only).

* cited by examiner

*Primary Examiner* — Mary Maille Lyons
(74) *Attorney, Agent, or Firm* — Oblon, McClelland, Maier & Neustadt, L.L.P.

(57) ABSTRACT

The present invention provides an agent for controlling colibacillosis including a fusion protein comprising a subunit of Shiga toxin and a subunit of *Escherichia coli* heat-labile toxin.

11 Claims, 5 Drawing Sheets

Fig. 1

Plasmid for expression in *Escherichia coli* (pET101)

Plasmid for expression in plants (pRI909)

L+  LTB PG12 HDEL

L-  LTB N90S PG12 HDEL

L+E-  LTB PG12 Stx2eBN73S PG12v2 HDEL

L-E-  LTB N90S PG12 Stx2eBN73S PG12v2 HDEL

E-L+  Stx2eBN73S PG12v2 LTB PG12 HDEL

E-L-  Stx2eBN73S PG12v2 LTB N90S PG12 HDEL

CBB staining

B

CBB staining

A

B

A

B

SEQUENCE LISTING

```
<160> NUMBER OF SEQ ID NOS: 49

<210> SEQ ID NO 1
<211> LENGTH: 36
<212> TYPE: DNA
<213> ORGANISM: Artificial Sequence
<220> FEATURE:
<223> OTHER INFORMATION: an artificially synthesized DNA

<400> SEQUENCE: 1
agatcccctg gttctggtcc tggttctcct agatcc                          36

<210> SEQ ID NO 2
<211> LENGTH: 12
<212> TYPE: PRT
<213> ORGANISM: Artificial Sequence
<220> FEATURE:
<223> OTHER INFORMATION: an artificially synthesized peptide
```

-continued

<400> SEQUENCE: 2

Arg Ser Pro Gly Ser Gly Pro Gly Ser Pro Arg Ser
1               5                   10

<210> SEQ ID NO 3
<211> LENGTH: 36
<212> TYPE: DNA
<213> ORGANISM: Artificial Sequence
<220> FEATURE:
<223> OTHER INFORMATION: an artificially synthesized DNA

<400> SEQUENCE: 3
agaggacctg gttctggtcc tggttctcct agatct                                36

<210> SEQ ID NO 4
<211> LENGTH: 12
<212> TYPE: PRT
<213> ORGANISM: Artificial Sequence
<220> FEATURE:
<223> OTHER INFORMATION: an artificially synthesized peptide

<400> SEQUENCE: 4

Arg Gly Pro Gly Ser Gly Pro Gly Ser Pro Arg Ser
1               5                   10

<210> SEQ ID NO 5
<211> LENGTH: 959
<212> TYPE: DNA
<213> ORGANISM: Escherichia coli

<400> SEQUENCE: 5
atgaagtgta tattgttaaa gtggatactg tgtctgttac tgggttttc ttcggtatcc        60
tattcccagg agtttacgat agactttcg actcaacaaa gttatgtatc ttcgttaaat       120
agtatacgga cagcgatatc gacccctctt gaacatatat ctcagggagc tacatcggta      180
tccgttatta atcatacacc accaggaagt tatatttccg taggtatacg agggcttgat      240
gtttatcagg agcgttttga ccatcttcgt ctgattattg aacgaaataa tttatatgtg      300
gctggatttg ttaatacgac aacaaatact ttctacagat tttcagattt gcacatatat      360
cattgcccgg tgtgacaact atttccatga caacggacag cagttatacc actctgcaac      420
gtgtcgcagc gctggaacgt tccggaatgc aaatcagtcg tcactcactg gtttcatcat      480
atctggcgtt aatggagttc agtggtaata caatgaccag agatgcatca agagcagttc      540
tgcgttttgt cactgtcaca gcagaagcct tacggttcag gcaaatacag agagaatttc      600
gtctggcact gtctgaaact gctcctgttt atacgatgac gccggaagac gtggacctca      660
ctctgaactg ggggagaatc agcaatgtgc ttccggagta tcgggagag gctggtgtca       720
gagtggggag aatatccttt aataatatat cagcgatact tggtactgtg gccgttatac      780
tgaattgcca tcatcagggc gcacgttctg ttcgcgccgt gaatgaagag agtcaaccag      840
aatgtcagat aactggcgac aggcccgtta taaaataaa caatacatta tgggaaagta       900
atacagcagc agcgtttctg aacagaaagt cacagccttt atatacaact ggtgaatga      959

<210> SEQ ID NO 6
<211> LENGTH: 304
<212> TYPE: PRT
<213> ORGANISM: Escherichia coli

<400> SEQUENCE: 6

Met Lys Cys Ile Leu Leu Lys Trp Ile Leu Cys Leu Leu Leu Gly Phe

```
  1               5                   10                  15
Ser Ser Val Ser Tyr Ser Gln Glu Phe Thr Ile Asp Phe Ser Thr Gln
              20                  25                  30

Gln Ser Tyr Val Ser Ser Leu Asn Ser Ala Ile Ser Thr Pro Leu Glu
              35                  40                  45

His Ile Ser Gln Gly Ala Thr Ser Val Ser Val Ile Asn His Thr Pro
 50                      55                  60

Pro Gly Ser Tyr Ile Ser Val Gly Ile Arg Gly Leu Asp Val Tyr Gln
 65                  70                  75                  80

Glu Arg Phe Asp His Leu Arg Leu Ile Ile Glu Arg Asn Asn Leu Tyr
                 85                  90                  95

Phe Val Asn Thr Thr Asn Thr Phe Tyr Arg Phe Ser Asp Phe Ala
                100                 105                 110

His Ile Ser Leu Pro Gly Val Thr Thr Ile Ser Met Thr Thr Asp Ser
                115                 120                 125

Ser Tyr Thr Thr Leu Gln Arg Val Ala Ala Leu Glu Arg Ser Gly Met
        130                 135                 140

Gln Ile Ser Arg His Ser Leu Tyr Leu Ala Leu Met Glu Phe Ser Gly
145                 150                 155                 160

Asn Thr Met Thr Arg Asp Ala Ser Arg Ala Val Leu Arg Phe Val Thr
                165                 170                 175

Val Thr Ala Glu Ala Leu Arg Phe Arg Gln Ile Gln Arg Glu Phe Arg
            180                 185                 190

Leu Ala Leu Ser Glu Thr Ala Pro Val Tyr Thr Met Thr Pro Asp Leu
        195                 200                 205

Thr Leu Asn Trp Gly Arg Ile Ser Asn Val Leu Pro Glu Tyr Arg Gly
210                 215                 220

Glu Ala Gly Val Arg Val Gly Arg Ile Ser Phe Asn Asn Ile Ser Ala
225                 230                 235                 240

Ile Leu Gly Thr Val Ala Val Ile Leu Asn Cys His His Gln Gly Ala
                245                 250                 255

Arg Ser Val Arg Ala Glu Ser Gln Pro Glu Cys Gln Ile Thr Gly Asp
            260                 265                 270

Arg Pro Val Ile Lys Ile Asn Asn Thr Leu Trp Glu Ser Asn Thr Ala
            275                 280                 285

Ala Ala Phe Leu Asn Arg Lys Ser Gln Pro Leu Tyr Thr Thr Gly Glu
        290                 295                 300

<210> SEQ ID NO 7
<211> LENGTH: 210
<212> TYPE: DNA
<213> ORGANISM: Escherichia coli

<400> SEQUENCE: 7
gcggcggact gcgcgaaggg caagatcgag ttctcgaagt acaacgagga caacacgttc      60
acggtcaagg tctcgggccg cgagtactgg acgaaccgct ggaacctgca gccgctgctg     120
cagtcggcgc agctgacggg catgacggtc acgatcatct cgaacacgtg ctcgtcgggc     180
tcgggcttcg cgcaggtcaa gttcaactga                                       210

<210> SEQ ID NO 8
<211> LENGTH: 69
<212> TYPE: PRT
<213> ORGANISM: Escherichia coli

<400> SEQUENCE: 8
```

```
Ala Ala Asp Cys Ala Lys Gly Lys Ile Glu Phe Ser Lys Tyr Asn Glu
1               5                   10                  15

Asp Asn Thr Phe Thr Val Lys Val Ser Gly Arg Glu Tyr Trp Thr Asn
            20                  25                  30

Arg Trp Asn Leu Gln Pro Leu Leu Gln Ser Ala Gln Leu Thr Gly Met
        35                  40                  45

Thr Val Thr Ile Ile Ser Asn Thr Cys Ser Ser Gly Ser Gly Phe Ala
        50                  55                  60

Gln Val Lys Phe Asn
65
```

<210> SEQ ID NO 9
<211> LENGTH: 210
<212> TYPE: DNA
<213> ORGANISM: Artificial Sequence
<220> FEATURE:
<223> OTHER INFORMATION: artificially synthesized polynucleotide

<400> SEQUENCE: 9

| | | |
|---|---|---|
| gcggcggact gcgcgaaggg caagatcgag ttctcgaagt acaacgagga caacacgttc | 60 |
| acggtcaagg tctcgggccg cgagtactgg acgaaccgct ggaacctgca gccgctgctg | 120 |
| cagtcggcgc agctgacggg catgacggtc acgatcatct cgtcgacgtg ctcgtcgggc | 180 |
| tcgggcttcg cgcaggtcaa gttcaactga | 210 |

<210> SEQ ID NO 10
<211> LENGTH: 69
<212> TYPE: PRT
<213> ORGANISM: Artificial Sequence
<220> FEATURE:
<223> OTHER INFORMATION: an artificially synthesized polypeptide

<400> SEQUENCE: 10

```
Ala Ala Asp Cys Ala Lys Gly Lys Ile Glu Phe Ser Lys Tyr Asn Glu
1               5                   10                  15

Asp Asn Thr Phe Thr Val Lys Val Ser Gly Arg Glu Tyr Trp Thr Asn
            20                  25                  30

Arg Trp Asn Leu Gln Pro Leu Leu Gln Ser Ala Gln Leu Thr Gly Met
        35                  40                  45

Thr Val Thr Ile Ile Ser Ser Thr Cys Ser Ser Gly Ser Gly Phe Ala
        50                  55                  60

Gln Val Lys Phe Asn
65
```

<210> SEQ ID NO 11
<211> LENGTH: 309
<212> TYPE: DNA
<213> ORGANISM: Escherichia coli

<400> SEQUENCE: 11

| | | |
|---|---|---|
| gcccccccaga ccatcaccga gttgtgcagc gagtaccgca cacccaaat ctacaccatc | 60 |
| aacgacaaga tcctcagcta caccgagagc atggccggca agagggagat ggtgatcatc | 120 |
| accttcaaga gcggcgagac cttccaggtc gaggtccccg cagccagca catcgacagc | 180 |
| cagaagaagg ccatcgagag gatgaaggac accctcagga tcacctacct caccgagacc | 240 |
| aagatcgaca agctctgcgt ctggaacaac aagacccca acagcatcgc cgccatcagc | 300 |
| atggagaac | 309 |

<210> SEQ ID NO 12
<211> LENGTH: 103
<212> TYPE: PRT
<213> ORGANISM: Escherichia coli

<400> SEQUENCE: 12

Ala Pro Gln Thr Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Glu Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn
            100

<210> SEQ ID NO 13
<211> LENGTH: 309
<212> TYPE: DNA
<213> ORGANISM: Artificial Sequence
<220> FEATURE:
<223> OTHER INFORMATION: an artificially synthesized polynucleotide

<400> SEQUENCE: 13
gccccccaga ccatcaccga gttgtgcagc gagtaccgca acacccaaat ctacaccatc      60
aacgacaaga tcctcagcta caccgagagc atggccggca agagggagat ggtgatcatc     120
accttcaaga gcggcgagac cttccaggtc gaggtccccg gcagccagca catcgacagc     180
cagaagaagg ccatcgagag gatgaaggac accctcagga tcacctacct caccgagacc     240
aagatcgaca agctctgcgt ctggaacagc aagaccccca acagcatcgc cgccatcagc     300
atggagaac                                                             309

<210> SEQ ID NO 14
<211> LENGTH: 103
<212> TYPE: PRT
<213> ORGANISM: Artificial Sequence
<220> FEATURE:
<223> OTHER INFORMATION: an artificially synthesized polypeptide

<400> SEQUENCE: 14

Ala Pro Gln Thr Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Glu Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Ser Lys Thr Pro Asn Ser Ile
                85                  90                  95

```
Ala Ala Ile Ser Met Glu Asn
            100

<210> SEQ ID NO 15
<211> LENGTH: 196
<212> TYPE: PRT
<213> ORGANISM: Artificial Sequence
<220> FEATURE:
<223> OTHER INFORMATION: an artificially synthesized polypeptide

<400> SEQUENCE: 15

Ala Pro Gln Thr Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Glu Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn Arg Ser Pro Gly Ser Gly Pro Gly Ser
            100                 105                 110

Pro Arg Ser Ala Ala Asp Cys Ala Lys Gly Lys Ile Glu Phe Ser Lys
        115                 120                 125

Tyr Asn Glu Asp Asn Thr Phe Thr Val Lys Val Ser Gly Arg Glu Tyr
    130                 135                 140

Trp Thr Asn Arg Trp Asn Leu Gln Pro Leu Leu Gln Ser Ala Gln Leu
145                 150                 155                 160

Thr Gly Met Thr Val Thr Ile Ile Ser Ser Thr Cys Ser Ser Gly Ser
                165                 170                 175

Gly Phe Ala Gln Val Lys Phe Asn Arg Gly Pro Gly Ser Gly Pro Gly
            180                 185                 190

Ser Pro Arg Ser
        195

<210> SEQ ID NO 16
<211> LENGTH: 196
<212> TYPE: PRT
<213> ORGANISM: Artificial Sequence
<220> FEATURE:
<223> OTHER INFORMATION: an artificially synthesized polypeptide

<400> SEQUENCE: 16

Ala Pro Gln Thr Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Glu Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Ser Lys Thr Pro Asn Ser Ile
                85                  90                  95
```

Ala Ala Ile Ser Met Glu Asn Arg Ser Pro Gly Ser Gly Pro Gly Ser
            100                 105                 110

Pro Arg Ser Ala Ala Asp Cys Ala Lys Gly Lys Ile Glu Phe Ser Lys
        115                 120                 125

Tyr Asn Glu Asp Asn Thr Phe Thr Val Lys Val Ser Gly Arg Glu Tyr
    130                 135                 140

Trp Thr Asn Arg Trp Asn Leu Gln Pro Leu Leu Gln Ser Ala Gln Leu
145                 150                 155                 160

Thr Gly Met Thr Val Thr Ile Ile Ser Ser Thr Cys Ser Ser Gly Ser
                165                 170                 175

Gly Phe Ala Gln Val Lys Phe Asn Arg Gly Pro Gly Ser Gly Pro Gly
            180                 185                 190

Ser Pro Arg Ser
        195

<210> SEQ ID NO 17
<211> LENGTH: 196
<212> TYPE: PRT
<213> ORGANISM: Artificial Sequence
<220> FEATURE:
<223> OTHER INFORMATION: an artificially synthesized polypeptide

<400> SEQUENCE: 17

Ala Ala Asp Cys Ala Lys Gly Lys Ile Glu Phe Ser Lys Tyr Asn Glu
1               5                   10                  15

Asp Asn Thr Phe Thr Val Lys Val Ser Gly Arg Glu Tyr Trp Thr Asn
            20                  25                  30

Arg Trp Asn Leu Gln Pro Leu Leu Gln Ser Ala Gln Leu Thr Gly Met
        35                  40                  45

Thr Val Thr Ile Ile Ser Ser Thr Cys Ser Ser Gly Ser Gly Phe Ala
    50                  55                  60

Gln Val Lys Phe Asn Arg Gly Pro Gly Ser Gly Pro Gly Ser Pro Arg
65                  70                  75                  80

Ser Ala Pro Gln Thr Ile Thr Glu Leu Cys Ser Glu Tyr Arg Asn Thr
                85                  90                  95

Gln Ile Tyr Thr Ile Asn Asp Lys Ile Leu Ser Tyr Thr Glu Ser Met
            100                 105                 110

Ala Gly Lys Arg Glu Met Val Ile Ile Thr Phe Lys Ser Gly Glu Thr
        115                 120                 125

Phe Gln Val Glu Val Pro Gly Ser Gln His Ile Asp Ser Gln Lys Lys
    130                 135                 140

Ala Ile Glu Arg Met Lys Asp Thr Leu Arg Ile Thr Tyr Leu Thr Glu
145                 150                 155                 160

Thr Lys Ile Asp Lys Leu Cys Val Trp Asn Asn Lys Thr Pro Asn Ser
                165                 170                 175

Ile Ala Ala Ile Ser Met Glu Asn Arg Ser Pro Gly Ser Gly Pro Gly
            180                 185                 190

Ser Pro Arg Ser
        195

<210> SEQ ID NO 18
<211> LENGTH: 196
<212> TYPE: PRT
<213> ORGANISM: Artificial Sequence
<220> FEATURE:
<223> OTHER INFORMATION: an artificially synthesized polypeptide

<400> SEQUENCE: 18

| Ala | Ala | Asp | Cys | Ala | Lys | Gly | Lys | Ile | Glu | Phe | Ser | Lys | Tyr | Asn | Glu |
|---|---|---|---|---|---|---|---|---|---|---|---|---|---|---|---|
| 1 | | | | 5 | | | | | 10 | | | | | 15 | |

| Asp | Asn | Thr | Phe | Thr | Val | Lys | Val | Ser | Gly | Arg | Glu | Tyr | Trp | Thr | Asn |
|---|---|---|---|---|---|---|---|---|---|---|---|---|---|---|---|
| | | | 20 | | | | | 25 | | | | | 30 | | |

| Arg | Trp | Asn | Leu | Gln | Pro | Leu | Leu | Gln | Ser | Ala | Gln | Leu | Thr | Gly | Met |
|---|---|---|---|---|---|---|---|---|---|---|---|---|---|---|---|
| | | 35 | | | | | 40 | | | | | 45 | | | |

| Thr | Val | Thr | Ile | Ile | Ser | Ser | Thr | Cys | Ser | Ser | Gly | Ser | Gly | Phe | Ala |
|---|---|---|---|---|---|---|---|---|---|---|---|---|---|---|---|
| | 50 | | | | | 55 | | | | | 60 | | | | |

| Gln | Val | Lys | Phe | Asn | Arg | Gly | Pro | Gly | Ser | Gly | Pro | Gly | Ser | Pro | Arg |
|---|---|---|---|---|---|---|---|---|---|---|---|---|---|---|---|
| 65 | | | | | 70 | | | | | 75 | | | | | 80 |

| Ser | Ala | Pro | Gln | Thr | Ile | Thr | Glu | Leu | Cys | Ser | Glu | Tyr | Arg | Asn | Thr |
|---|---|---|---|---|---|---|---|---|---|---|---|---|---|---|---|
| | | | 85 | | | | | 90 | | | | | 95 | | |

| Gln | Ile | Tyr | Thr | Ile | Asn | Asp | Lys | Ile | Leu | Ser | Tyr | Thr | Glu | Ser | Met |
|---|---|---|---|---|---|---|---|---|---|---|---|---|---|---|---|
| | | | 100 | | | | | 105 | | | | | 110 | | |

| Ala | Gly | Lys | Arg | Glu | Met | Val | Ile | Ile | Thr | Phe | Lys | Ser | Gly | Glu | Thr |
|---|---|---|---|---|---|---|---|---|---|---|---|---|---|---|---|
| | | | 115 | | | | | 120 | | | | | 125 | | |

| Phe | Gln | Val | Glu | Val | Pro | Gly | Ser | Gln | His | Ile | Asp | Ser | Gln | Lys | Lys |
|---|---|---|---|---|---|---|---|---|---|---|---|---|---|---|---|
| | 130 | | | | | 135 | | | | | 140 | | | | |

| Ala | Ile | Glu | Arg | Met | Lys | Asp | Thr | Leu | Arg | Ile | Thr | Tyr | Leu | Thr | Glu |
|---|---|---|---|---|---|---|---|---|---|---|---|---|---|---|---|
| 145 | | | | | 150 | | | | | 155 | | | | | 160 |

| Thr | Lys | Ile | Asp | Lys | Leu | Cys | Val | Trp | Asn | Ser | Lys | Thr | Pro | Asn | Ser |
|---|---|---|---|---|---|---|---|---|---|---|---|---|---|---|---|
| | | | 165 | | | | | 170 | | | | | 175 | | |

| Ile | Ala | Ala | Ile | Ser | Met | Glu | Asn | Arg | Ser | Pro | Gly | Ser | Gly | Pro | Gly |
|---|---|---|---|---|---|---|---|---|---|---|---|---|---|---|---|
| | | | 180 | | | | | 185 | | | | | 190 | | |

| Ser | Pro | Arg | Ser |
|---|---|---|---|
| | | | 195 |

<210> SEQ ID NO 19
<211> LENGTH: 588
<212> TYPE: DNA
<213> ORGANISM: Artificial Sequence
<220> FEATURE:
<223> OTHER INFORMATION: an artificially synthesized polynucleotide

<400> SEQUENCE: 19

```
gcccccaga ccatcaccga gttgtgcagc gagtaccgca acacccaaat ctacaccatc     60
aacgacaaga tcctcagcta caccgagagc atggccggag agaggagat ggtgatcatc    120
accttcaaga gcggcgagac cttccaggtc gaggtccccg gcagccagca catcgacagc    180
cagaagaagg ccatcgagag gatgaaggac accctcagga tcacctacct caccgagacc    240
aagatcgaca agctctgcgt ctggaacaac aagacccca acagcatcgc cgccatcagc    300
atggagaaca gatcccctgg ttctggtcct ggttctccta gatccgcggc ggactgcgcg    360
aagggcaaga tcgagttctc gaagtacaac gaggacaaca cgttcacggt caaggtctcg    420
ggccgcgagt actggacgaa ccgctggaac ctgcagccgc tgctgcagtc ggcgcagctg    480
acgggcatga cggtcacgat catctcgtcg acgtgctcgt cgggctcggg cttcgcgcag    540
gtcaagttca acagaggacc tggttctggt cctggttctc ctagatct                588
```

<210> SEQ ID NO 20
<211> LENGTH: 588
<212> TYPE: DNA
<213> ORGANISM: Artificial Sequence
<220> FEATURE:
<223> OTHER INFORMATION: an artificially synthesized polynucleotide

<400> SEQUENCE: 20

```
gcccccaga ccatcaccga gttgtgcagc gagtaccgca acacccaaat ctacaccatc    60
aacgacaaga tcctcagcta caccgagagc atggccggca agagggagat ggtgatcatc   120
accttcaaga gcggcgagac cttccaggtc gaggtccccg gcagccagca catcgacagc   180
cagaagaagg ccatcgagag gatgaaggac accctcagga tcacctacct caccgagacc   240
aagatcgaca agctctgcgt ctggaacagc aagaccccca acagcatcgc cgccatcagc   300
atggagaaca gatcccctgg ttctggtcct ggttctccta gatccgcggc ggactgcgcg   360
aagggcaaga tcgagttctc gaagtacaac gaggacaaca cgttcacggt caaggtctcg   420
ggccgcgagt actggacgaa ccgctggaac ctgcagccgc tgctgcagtc ggcgcagctg   480
acgggcatga cggtcacgat catctcgtcg acgtgctcgt cgggctcggg cttcgcgcag   540
gtcaagttca acagaggacc tggttctggt cctggttctc ctagatct               588
```

<210> SEQ ID NO 21
<211> LENGTH: 588
<212> TYPE: DNA
<213> ORGANISM: Artificial Sequence
<220> FEATURE:
<223> OTHER INFORMATION: an artificially synthesized polynucleotide

<400> SEQUENCE: 21

```
gcggcggact gcgcgaaggg caagatcgag ttctcgaagt acaacgagga caacacgttc    60
acggtcaagg tctcgggccg cgagtactgg acgaaccgct ggaacctgca gccgctgctg   120
cagtcggcgc agctgacggg catgacggtc acgatcatct cgtcgacgtg ctcgtcgggc   180
tcgggcttcg cgcaggtcaa gttcaacaga ggacctggtt ctggtcctgg ttctcctaga   240
tccgcccccc agaccatcac cgagttgtgc agcgagtacc gcaacaccca aatctacacc   300
atcaacgaca agatcctcag ctacaccgag agcatggccg gcaagaggga gatggtgatc   360
atcaccttca gagcggcga gaccttccag gtcgaggtcc ccggcagcca gcacatcgac   420
agccagaaga aggccatcga gaggatgaag gacaccctca ggatcaccta cctcaccgag   480
accaagatcg acaagctctg cgtctggaac aacaagaccc ccaacagcat cgccgccatc   540
agcatggaga acagatcccc tggttctggt cctggttctc ctagatct               588
```

<210> SEQ ID NO 22
<211> LENGTH: 588
<212> TYPE: DNA
<213> ORGANISM: Artificial Sequence
<220> FEATURE:
<223> OTHER INFORMATION: an artificially synthesized polynucleotide

<400> SEQUENCE: 22

```
gcggcggact gcgcgaaggg caagatcgag ttctcgaagt acaacgagga caacacgttc    60
acggtcaagg tctcgggccg cgagtactgg acgaaccgct ggaacctgca gccgctgctg   120
cagtcggcgc agctgacggg catgacggtc acgatcatct cgtcgacgtg ctcgtcgggc   180
tcgggcttcg cgcaggtcaa gttcaacaga ggacctggtt ctggtcctgg ttctcctaga   240
tccgcccccc agaccatcac cgagttgtgc agcgagtacc gcaacaccca aatctacacc   300
atcaacgaca agatcctcag ctacaccgag agcatggccg gcaagaggga gatggtgatc   360
atcaccttca gagcggcga gaccttccag gtcgaggtcc ccggcagcca gcacatcgac   420
agccagaaga aggccatcga gaggatgaag gacaccctca ggatcaccta cctcaccgag   480
accaagatcg acaagctctg cgtctggaac agcaagaccc ccaacagcat cgccgccatc   540
```
agcatggaga acagatcccc tggttctggt cctggttctc ctagatct        588

<210> SEQ ID NO 23
<211> LENGTH: 772
<212> TYPE: DNA
<213> ORGANISM: Artificial Sequence
<220> FEATURE:
<223> OTHER INFORMATION: an artificially synthesized DNA construct

<400> SEQUENCE: 23
tatttaactc agtattcaga acaacaaaa gttcttctct acataaaatt ttcctatttt        60
agtgatcagt gaaggaaatc aagaaaaaaa gatggggaga atgtcaatac ccatgatggg       120
ttttgtggtg ttatgtctat gggcagtggt agcagaagga ggatccgccc cccagaccat       180
caccgagttg tgcagcgagt accgcaacac ccaaatctac accatcaacg acaagatcct       240
cagctacacc gagagcatgg ccggcaagag ggagatggtg atcatcacct tcaagagcgg       300
cgagaccttc caggtcgagg tccccggcag ccagcacatc gacagccaga agaaggccat       360
cgagaggatg aaggacaccc tcaggatcac ctacctcacc gagaccaaga tcgacaagct       420
ctgcgtctgg aacaacaaga cccccaacag catcgccgcc atcagcatgg agaacagatc       480
ccctggttct ggtcctggtt ctcctagatc cgcggcggac tgcgcgaagg gcaagatcga       540
gttctcgaag tacaacgagg acaacacgtt cacggtcaag gtctcgggcc gcgagtactg       600
gacgaaccgc tggaacctgc agccgctgct gcagtcggcg cagctgacgg gcatgacggt       660
cacgatcatc tcgtcgacgt gctcgtcggg ctcgggcttc gcgcaggtca agttcaacag       720
aggacctggt tctggtcctg gttctcctag atctgaacat gatgaattgt ga              772

<210> SEQ ID NO 24
<211> LENGTH: 772
<212> TYPE: DNA
<213> ORGANISM: Artificial Sequence
<220> FEATURE:
<223> OTHER INFORMATION: an artificially synthesized DNA construct

<400> SEQUENCE: 24
tatttaactc agtattcaga acaacaaaa gttcttctct acataaaatt ttcctatttt        60
agtgatcagt gaaggaaatc aagaaaaaaa gatggggaga atgtcaatac ccatgatggg       120
ttttgtggtg ttatgtctat gggcagtggt agcagaagga ggatccgccc cccagaccat       180
caccgagttg tgcagcgagt accgcaacac ccaaatctac accatcaacg acaagatcct       240
cagctacacc gagagcatgg ccggcaagag ggagatggtg atcatcacct tcaagagcgg       300
cgagaccttc caggtcgagg tccccggcag ccagcacatc gacagccaga agaaggccat       360
cgagaggatg aaggacaccc tcaggatcac ctacctcacc gagaccaaga tcgacaagct       420
ctgcgtctgg aacagcaaga cccccaacag catcgccgcc atcagcatgg agaacagatc       480
ccctggttct ggtcctggtt ctcctagatc cgcggcggac tgcgcgaagg gcaagatcga       540
gttctcgaag tacaacgagg acaacacgtt cacggtcaag gtctcgggcc gcgagtactg       600
gacgaaccgc tggaacctgc agccgctgct gcagtcggcg cagctgacgg gcatgacggt       660
cacgatcatc tcgtcgacgt gctcgtcggg ctcgggcttc gcgcaggtca agttcaacag       720
aggacctggt tctggtcctg gttctcctag atctgaacat gatgaattgt ga              772

<210> SEQ ID NO 25
<211> LENGTH: 772
<212> TYPE: DNA

<213> ORGANISM: Artificial Sequence
<220> FEATURE:
<223> OTHER INFORMATION: an artificially synthesized DNA construct

<400> SEQUENCE: 25

```
tatttaactc agtattcaga acaacaaaa gttcttctct acataaaatt ttcctatttt      60
agtgatcagt gaaggaaatc aagaaaaaaa gatggggaga atgtcaatac ccatgatggg    120
ttttgtggtg ttatgtctat ggcagtggt agcagaagga ggatccgcgg cggactgcgc     180
gaagggcaag atcgagttct cgaagtacaa cgaggacaac acgttcacgg tcaaggtctc    240
gggccgcgag tactggacga accgctggaa cctgcagccg ctgctgcagt cggcgcagct    300
gacgggcatg acggtcacga tcatctcgtc gacgtgctcg tcgggctcgg gcttcgcgca    360
ggtcaagttc aacagaggac ctggttctgg tcctggttct cctagatccg cccccccagac  420
catcaccgag ttgtgcagcg agtaccgcaa cacccaaatc tacaccatca acgacaagat   480
cctcagctac accgagagca tggccggcaa gagggagatg gtgatcatca ccttcaagag   540
cggcgagacc ttccaggtcg aggtccccgg cagccagcac atcgacagcc agaagaaggc   600
catcgagagg atgaaggaca ccctcaggat cacctacctc accgagacca agatcgacaa   660
gctctgcgtc tggaacaaca agacccccaa cagcatcgcc gccatcagca tggagaacag   720
atcccctggt tctggtcctg gttctcctag atctgaacat gatgaattgt ga           772
```

<210> SEQ ID NO 26
<211> LENGTH: 772
<212> TYPE: DNA
<213> ORGANISM: Artificial Sequence
<220> FEATURE:
<223> OTHER INFORMATION: an artificially synthesized DNA construct

<400> SEQUENCE: 26

```
tatttaactc agtattcaga acaacaaaa gttcttctct acataaaatt ttcctatttt      60
agtgatcagt gaaggaaatc aagaaaaaaa gatggggaga atgtcaatac ccatgatggg    120
ttttgtggtg ttatgtctat ggcagtggt agcagaagga ggatccgcgg cggactgcgc     180
gaagggcaag atcgagttct cgaagtacaa cgaggacaac acgttcacgg tcaaggtctc    240
gggccgcgag tactggacga accgctggaa cctgcagccg ctgctgcagt cggcgcagct    300
gacgggcatg acggtcacga tcatctcgtc gacgtgctcg tcgggctcgg gcttcgcgca    360
ggtcaagttc aacagaggac ctggttctgg tcctggttct cctagatccg cccccccagac  420
catcaccgag ttgtgcagcg agtaccgcaa cacccaaatc tacaccatca acgacaagat   480
cctcagctac accgagagca tggccggcaa gagggagatg gtgatcatca ccttcaagag   540
cggcgagacc ttccaggtcg aggtccccgg cagccagcac atcgacagcc agaagaaggc   600
catcgagagg atgaaggaca ccctcaggat cacctacctc accgagacca agatcgacaa   660
gctctgcgtc tggaacagca agacccccaa cagcatcgcc gccatcagca tggagaacag   720
atcccctggt tctggtcctg gttctcctag atctgaacat gatgaattgt ga           772
```

<210> SEQ ID NO 27
<211> LENGTH: 72
<212> TYPE: DNA
<213> ORGANISM: Nicotiana tabacum

<400> SEQUENCE: 27

```
atggggagaa tgtcaatacc catgatgggt tttgtggtgt tatgtctatg gcagtggta     60
gcagaaggat cc                                                        72
```

<210> SEQ ID NO 28
<211> LENGTH: 24
<212> TYPE: PRT
<213> ORGANISM: Nicotiana tabacum

<400> SEQUENCE: 28

Met Gly Arg Met Ser Ile Pro Met Met Gly Phe Val Val Leu Cys Leu
1               5                   10                  15

Trp Ala Val Val Ala Glu Gly Ser
            20

<210> SEQ ID NO 29
<211> LENGTH: 4
<212> TYPE: PRT
<213> ORGANISM: Artificial Sequence
<220> FEATURE:
<223> OTHER INFORMATION: an artificially synthesized peptide

<400> SEQUENCE: 29

His Asp Glu Leu
1

<210> SEQ ID NO 30
<211> LENGTH: 91
<212> TYPE: DNA
<213> ORGANISM: Nicotiana tabacum

<400> SEQUENCE: 30
tatttaactc agtattcaga acaacaaaa gttcttctct acataaaatt ttcctatttt    60
agtgatcagt gaaggaaatc aagaaaaata a                                  91

<210> SEQ ID NO 31
<211> LENGTH: 91
<212> TYPE: DNA
<213> ORGANISM: Nicotiana tabacum

<400> SEQUENCE: 31
tatttaactc agtattcaga acaacaaaa gttcttctct acataaaatt ttcctatttt    60
agtgatcagt gaaggaaatc aagaaaaaaa g                                  91

<210> SEQ ID NO 32
<211> LENGTH: 256
<212> TYPE: DNA
<213> ORGANISM: Arabidopsis thaliana

<400> SEQUENCE: 32
atatgaagat gaagatgaaa tatttggtgt gtcaaataaa aagctagctt gtgtgcttaa    60
gtttgtgttt ttttcttggc ttgttgtgtt atgaatttgt ggctttttct aatattaaat   120
gaatgtaaga tctcattata atgaataaac aaatgtttct ataatccatt gtgaatgttt   180
tgttggatct cttcgcatat aactactgta tgtgctatgg tatggactat ggaatatgat   240
taaagataag actagt                                                   256

<210> SEQ ID NO 33
<211> LENGTH: 35
<212> TYPE: DNA
<213> ORGANISM: Artificial Sequence
<220> FEATURE:
<223> OTHER INFORMATION: an artificially synthesized primer

<400> SEQUENCE: 33
aaatctagaa ataataagga gttaagaatg aagaa                              35

<210> SEQ ID NO 34
<211> LENGTH: 33
<212> TYPE: DNA
<213> ORGANISM: Artificial Sequence
<220> FEATURE:
<223> OTHER INFORMATION: an artificially synthesized primer

<400> SEQUENCE: 34
aaaggatcct gcattaacag aaaccaatgc aaa                                33

<210> SEQ ID NO 35
<211> LENGTH: 44
<212> TYPE: DNA
<213> ORGANISM: Artificial Sequence
<220> FEATURE:
<223> OTHER INFORMATION: an artificially synthesized primer

<400> SEQUENCE: 35
ttggatccgc cccccagacc atcaccgagt tgtgcagcga gtac                    44

<210> SEQ ID NO 36
<211> LENGTH: 39
<212> TYPE: DNA
<213> ORGANISM: Artificial Sequence
<220> FEATURE:
<223> OTHER INFORMATION: an artificially synthesized primer

<400> SEQUENCE: 36
cgttgatggt gtagatttgg gtgttgcggt actcgctgc                          39

<210> SEQ ID NO 37
<211> LENGTH: 39
<212> TYPE: DNA
<213> ORGANISM: Artificial Sequence
<220> FEATURE:
<223> OTHER INFORMATION: an artificially synthesized primer

<400> SEQUENCE: 37
ccatcaacga caagatcctc agctacaccg agagcatgg                          39

<210> SEQ ID NO 38
<211> LENGTH: 43
<212> TYPE: DNA
<213> ORGANISM: Artificial Sequence
<220> FEATURE:
<223> OTHER INFORMATION: an artificially synthesized primer

<400> SEQUENCE: 38
cttgaaggtg atgatcacca tctccctctt gccggccatg ctc                     43

<210> SEQ ID NO 39
<211> LENGTH: 39
<212> TYPE: DNA
<213> ORGANISM: Artificial Sequence
<220> FEATURE:
<223> OTHER INFORMATION: an artificially synthesized primer

<400> SEQUENCE: 39
atcaccttca agagcggcga gaccttccag gtcgaggtc                          39

<210> SEQ ID NO 40
<211> LENGTH: 45
<212> TYPE: DNA

```
<213> ORGANISM: Artificial Sequence
<220> FEATURE:
<223> OTHER INFORMATION: an artificially synthesized primer

<400> SEQUENCE: 40
cttctggctg tcgatgtgct ggctgccggg gacctcgacc tggaa                    45

<210> SEQ ID NO 41
<211> LENGTH: 48
<212> TYPE: DNA
<213> ORGANISM: Artificial Sequence
<220> FEATURE:
<223> OTHER INFORMATION: an artificially synthesized primer

<400> SEQUENCE: 41
gacagccaga agaaggccat cgagaggatg aaggacaccc tcaggatc                 48

<210> SEQ ID NO 42
<211> LENGTH: 44
<212> TYPE: DNA
<213> ORGANISM: Artificial Sequence
<220> FEATURE:
<223> OTHER INFORMATION: an artificially synthesized primer

<400> SEQUENCE: 42
gcagagcttg tcgatcttgg tctcggtgag gtaggtgatc ctga                     44

<210> SEQ ID NO 43
<211> LENGTH: 30
<212> TYPE: DNA
<213> ORGANISM: Artificial Sequence
<220> FEATURE:
<223> OTHER INFORMATION: an artificially synthesized primer

<400> SEQUENCE: 43
aagctctgcg tctggaacaa caagaccccc                                     30

<210> SEQ ID NO 44
<211> LENGTH: 68
<212> TYPE: DNA
<213> ORGANISM: Artificial Sequence
<220> FEATURE:
<223> OTHER INFORMATION: an artificially synthesized primer

<400> SEQUENCE: 44
aaagatctgt tctccatgct gatggcggcg atgctgttgg gggtcttgtt gttccagacg    60
cagagctt                                                             68

<210> SEQ ID NO 45
<211> LENGTH: 30
<212> TYPE: DNA
<213> ORGANISM: Artificial Sequence
<220> FEATURE:
<223> OTHER INFORMATION: an artificially synthesized primer

<400> SEQUENCE: 45
aagctctgcg tctggaacag caagaccccc                                     30

<210> SEQ ID NO 46
<211> LENGTH: 30
<212> TYPE: DNA
<213> ORGANISM: Artificial Sequence
<220> FEATURE:
<223> OTHER INFORMATION: an aritificially synthesized primer

<400> SEQUENCE: 46
```

```
gatccectgg ttctggtcct ggttctccta                                    30

<210> SEQ ID NO 47
<211> LENGTH: 30
<212> TYPE: DNA
<213> ORGANISM: Artificial Sequence
<220> FEATURE:
<223> OTHER INFORMATION: an aritificially synthesized primer

<400> SEQUENCE: 47
gatctaggag aaccaggacc agaaccaggg                                    30

<210> SEQ ID NO 48
<211> LENGTH: 59
<212> TYPE: DNA
<213> ORGANISM: Artificial Sequence
<220> FEATURE:
<223> OTHER INFORMATION: an artificially synthesized primer

<400> SEQUENCE: 48
aaggatccgc ggcggactgc gcgaagggca agatcgagtt ctcgaagtac aacgaggac    59

<210> SEQ ID NO 49
<211> LENGTH: 38
<212> TYPE: DNA
<213> ORGANISM: Artificial Sequence
<220> FEATURE:
<223> OTHER INFORMATION: an artificially synthesized primer

<400> SEQUENCE: 49
aaagatctag gagaaccagg accagaacca ggtcctct                           38
```

VACCINE AGAINST COLIBACILLOSIS

TECHNICAL FIELD

The present invention relates to a controlling agent with preventive and therapeutic effects against colibacillosis.

BACKGROUND ART

Microbial pathogens may infect their host through one of several mechanisms. These microbial pathogens may enter their host through wounds on the skin, or via interaction with mucosal surfaces. Bacterial pathogens and viral pathogens which affect the host through this mechanism first come in contact with a mucosal surface, adhere thereto, and then colonize thereon, or are taken up by specialized absorptive cells (M cells) which exist inside the epithelium over Peyer's patches and other lymphoid follicles.

A secretory IgA (sIgA) antibody which acts against the specific virulence determinant of infecting organisms plays a major role in mucosal immunity. In many cases, initial infection can be prevented by boosting the production of mucosal sIgA antibody which acts against the associated virulence determinant of the infecting organisms. The secretory IgA antibody is capable of preventing the initial interaction between the pathogens and mucosal surfaces by blocking their attachment and/or colonization, neutralizing surface-acting toxins, or by blocking their entry into host cells.

Edema disease of swine frequently develops in post-weaning pigs, due to infection with *Escherichia coli*. Although antibiotics are used for the prevention and treatment of edema disease of swine, it is an urgent matter to develop a preventive approach which could replace conventional methods using antibiotics, because of concerns for food safety and the emergence of resistant bacteria. However, there is no effective vaccine for edema disease at present. *Escherichia coli* diarrhea develops in young pigs during the lactation period and immediately after weaning. Although vaccines for use in the lactation period, designed to be administered to mother pigs, are commercially available, they cannot protect young pigs against diarrhea during the weaning period when maternal antibodies are starting to wear off. In addition, vaccines for preventing diarrhea which occurs during the weaning period are not commercially available. Thus, it is considered to be very useful to develop an orally administrable vaccine which is capable of preventing these diseases at the same time.

Patent Document 1 discloses the transformation of *Arabidopsis thaliana* cultured cells and a fragment of lettuce leaves in such a way that modified B subunit of edema disease toxin (Stx2eB) in which glycosylation is inhibited is transiently expressed. However, the effect of Stx2eB produced in the transformant when it is actually used as a vaccine has not been confirmed.

Patent Document 2 discloses a technique to link a vaccine antigen(s) for edema disease of swine and an antigen(s) for *Escherichia coli* diarrhea, to achieve a high accumulation of target proteins in a transgenic plant. However, in Patent Document 2, an issue that whether the above mentioned transgenic plant can be actually used as a vaccine or not remains unconfirmed. Further, Patent Document 2 is silent about the effects of: (1) the arrangement order in which a B subunit(s) of *Escherichia coli* heat-labile toxin (LTB) and a Stx2eB (s) are fused; and (2) the addition of an N-linked sugar chain to the LTB, on the level of antigen accumulation in plant cells, and on the performance as a vaccine.

Non-patent Document 1 discloses the expression and purification of a Stx2eB-LTB fusion antigen using recombinant *Escherichia coli*, and the evaluation of its performance. However, the performance evaluation of the fusion antigen when expressed in a plant such as strawberry and lettuce as a host is not described therein. Further, in Non-patent Document 1, the effect of the arrangement order in which LTB and Stx2eB are fused on the level of antigen accumulation in plant cells and on the performance as a vaccine has not been examined. In addition, although the effect of the Stx2eB-LTB fusion antigen to protect against Stx2e toxin has been confirmed, its effect in terms of protecting against LT toxin has not been evaluated. Moreover, Non-patent Document 1 describes the administration of the fusion antigen to an animal by injection (with the addition of an adjuvant), and it has not been confirmed whether or not the induction of immunity is possible by oral administration (without the addition of an adjuvant), which is an easier and more cost effective method.

PRIOR ART DOCUMENTS

Patent Documents

Patent Document 1: JP 2012-19719 A
Patent Document 2: WO 2009/133882 A

Non-Patent Documents

Non-patent Document 1: Ran et al., Veterinary Microbiology 127 (2008) 209-15

SUMMARY OF THE INVENTION

Problems to be Solved by the Invention

An object of the present invention is to optimize the accumulation of antigen in plant cells and the performance of controlling colibacillosis (vaccine effect, immunostimulating effect, or therapeutic effect) in an agent for controlling colibacillosis comprising a subunit of *Escherichia coli* heat-labile toxin (LT) and a subunit of edema disease (Stx2e).

Means for Solving the Problems

The present inventors have engaged in intensive studies to solve the above mentioned problems, and discovered as a result that an agent for controlling colibacillosis comprising a B subunit of *Escherichia coli* heat-labile toxin (LTB) and a B subunit of edema disease toxin (Stx2eB) is more effective in preventing both edema disease of swine and *Escherichia coli* diarrhea, as compared to controlling agents comprising one of the above mentioned subunits alone.

Further, the present inventors have discovered that the addition of an N-linked sugar chain to Asn residue at position 90 in the B subunit of *Escherichia coli* heat-labile toxin (LTB) allows for increasing the production of the target protein in plant cells, and for improving the efficiency as the controlling agent (vaccine effect, immunostimulating effect, or therapeutic effect).

The present inventors have thereby completed the present invention.

The present invention provide the followings.
(1) An agent for controlling colibacillosis comprising a fusion protein comprising a subunit of Shiga toxin and a subunit of *Escherichia coli* heat-labile toxin.

(2) The agent for controlling colibacillosis according to (1), wherein the subunit of Shiga toxin and the subunit of *Escherichia coli* heat-labile toxin have been fused via a peptide linker.
(3) The agent for controlling colibacillosis according to (1) or (2), wherein each of the subunit of Shiga toxin and the subunit of *Escherichia coli* heat-labile toxin is a B subunit.
(4) The agent for controlling colibacillosis according to (3), wherein Asn residue at position 73 in the B subunit of the Shiga toxin has been replaced by Ser.
(5) The agent for controlling colibacillosis according to (3) or (4), wherein a sugar chain has been added to the B subunit of *Escherichia coli* heat-labile toxin.
(6) The agent for controlling colibacillosis according to (5), wherein an N-linked sugar chain has been added to Asn residue at position 90 of the B subunit of *Escherichia coli* heat-labile toxin.
(7) The agent for controlling colibacillosis according to any one of (1) to (6), wherein the *Escherichia coli* heat-labile toxin has been fused to the C terminus side of the Shiga toxin.
(8) The agent for controlling colibacillosis according to any one of (1) to (6), wherein the *Escherichia coli* heat-labile toxin has been fused to the N terminus side of the Shiga toxin.
(9) The agent for controlling colibacillosis according to any one of (1) to (8), wherein the agent is a protein antigen or an immunostimulant that induces antibodies against the *Escherichia coli* heat-labile toxin.
(10) The agent for controlling colibacillosis according to (9), wherein the agent is a protein antigen or an immunostimulant that induces IgA.
(11) The agent for controlling colibacillosis according to (9), wherein the agent is a protein antigen or an immunostimulant that induces IgG.
(12) The agent for controlling colibacillosis according to any one of (1) to (11), wherein the colibacillosis is *Escherichia coli* diarrhea.
(13) The agent for controlling colibacillosis according to (12), wherein the colibacillosis is both edema disease of swine and *Escherichia coli* diarrhea.
(14) A feed comprising the agent for controlling colibacillosis according to any one of (1) to (13).
(15) A method for controlling colibacillosis in a non-human animal, the method comprising administering an edible plant transformed with a recombinant vector including a DNA construct containing a DNA which codes for a fusion protein comprising a subunit of Shiga toxin and a subunit of *Escherichia coli* heat-labile toxin.
(16) A fusion protein comprising a subunit of Shiga toxin and a subunit of *Escherichia coli* heat-labile toxin, for use in controlling colibacillosis.
(17) Use of a fusion protein comprising a subunit of Shiga toxin and a subunit of *Escherichia coli* heat-labile toxin, for producing an agent for controlling colibacillosis.

Effect of the Invention

In the agent for controlling colibacillosis according to the present invention, the accumulation of antigen in plant cells and the performance of controlling colibacillosis (vaccine effect, immunostimulating effect, or therapeutic effect) are markedly improved, as compared to vaccines disclosed in prior art documents.
The agent for controlling colibacillosis according to the present invention allows for preventing both edema disease of swine and *Escherichia coli* diarrhea at the same time.

Since, in the present invention, protein antigens are accumulated in an edible plant to be administered orally, an increased productivity in livestock farming can be expected due to the reduction in the cost, the consumption of power, and the stress in farm animals.
The agent for controlling colibacillosis according to the present invention is capable of preventing or treating the symptoms of colibacillosis. When the agent for controlling colibacillosis according to the present invention is administered to a healthy non-human animal, an effect as a vaccine or an immunostimulant can be expected.

BRIEF DESCRIPTION OF THE DRAWINGS

FIG. 1 is a diagram illustrating the constructs for expression of an agent for controlling colibacillosis according to the present invention.
FIG. 2A illustrates the results of the purification of fusion proteins using a galactose column (electrophoresis images).
FIG. 2B illustrates the results of the electrophoresis of the purified fusion proteins with or without heat denaturation (electrophoresis images).
FIG. 8A shows a time table. Three pigs were selected for respective groups. Those in a negative control group were administered with lettuce prepared with empty vector.
FIG. 8B is a graph illustrating the clinical scores. Each of the clinical scores was obtained by adding up the score values of from the first day of challenge (25-day old) to the day of autopsy (34-day old). The data indicate the mean values and the standard deviations of three pigs in the respective groups.
FIG. 8C is a graph illustrating the percentage of body weight increase from the first day of challenge until the day of autopsy (the body weight on the first day of challenge was used as a reference). The data indicate the mean values and the standard deviations of three pigs in the respective groups. No administration of the lettuce or challenge was carried out for healthy pigs.

EMBODIMENTS FOR CARRYING OUT THE INVENTION

Figure 3:
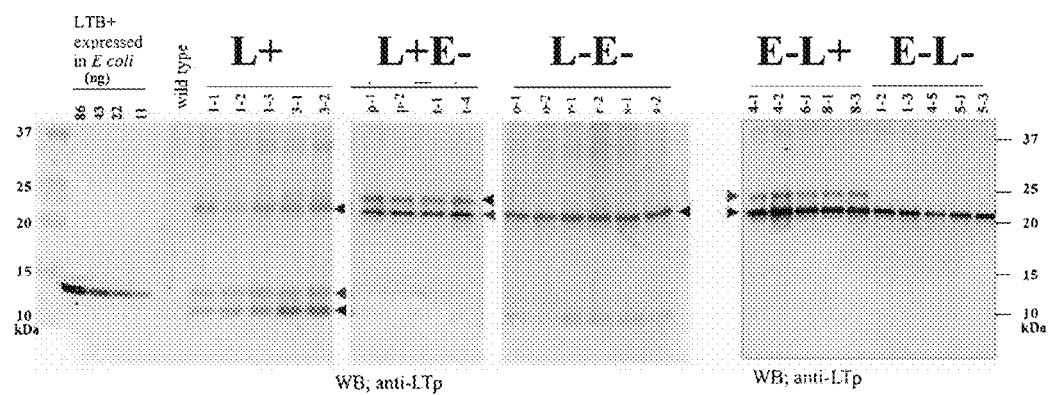
FIG. 3A illustrates the accumulation of the fusion proteins in lettuces (electrophoresis images).
FIG. 3B shows the amounts of the fusion proteins accumulated in respective transgenic lettuces.
Figure 3:
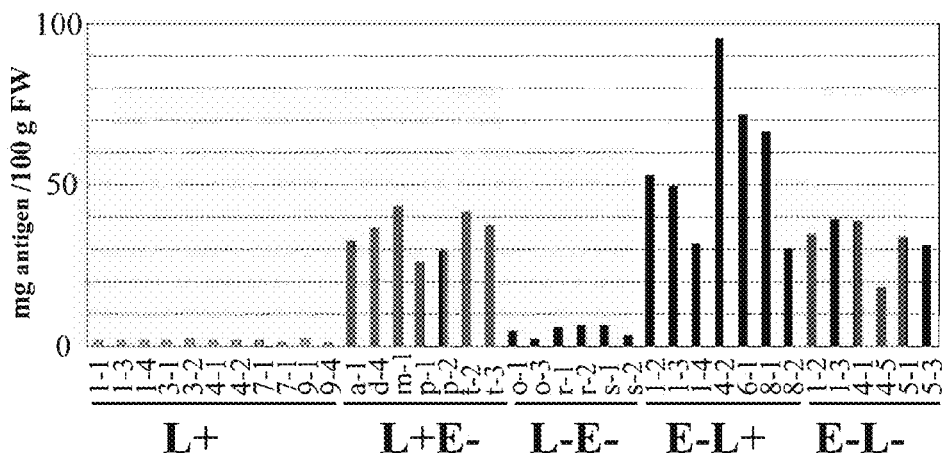
Figure 4:
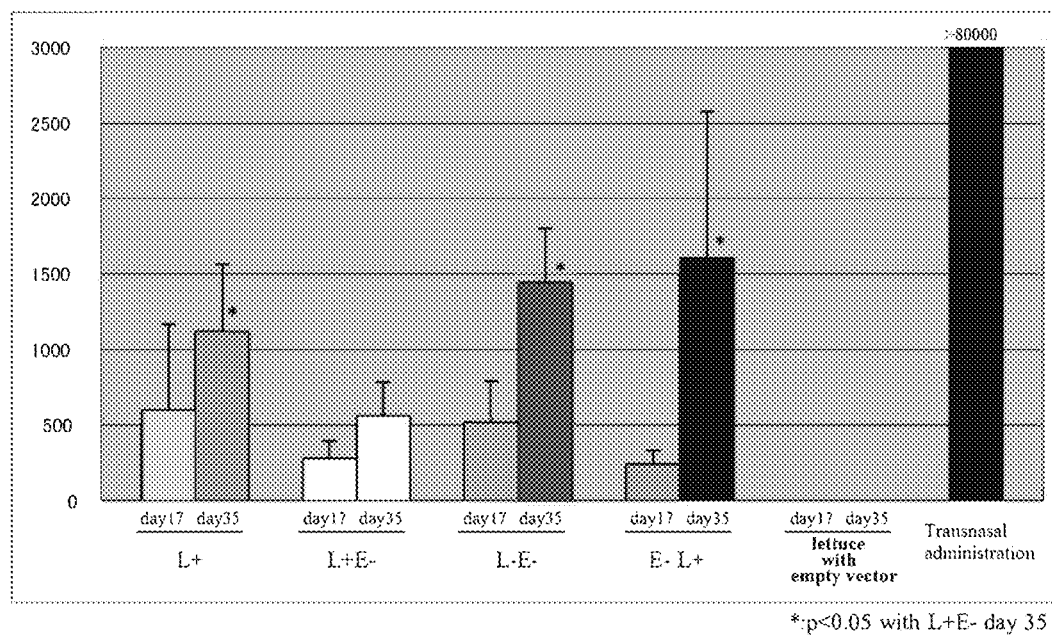
FIG. 4 is a graph illustrating the anti-IgG antibody titer in the serum of mice orally administered with transformed plants.
Figure 5:
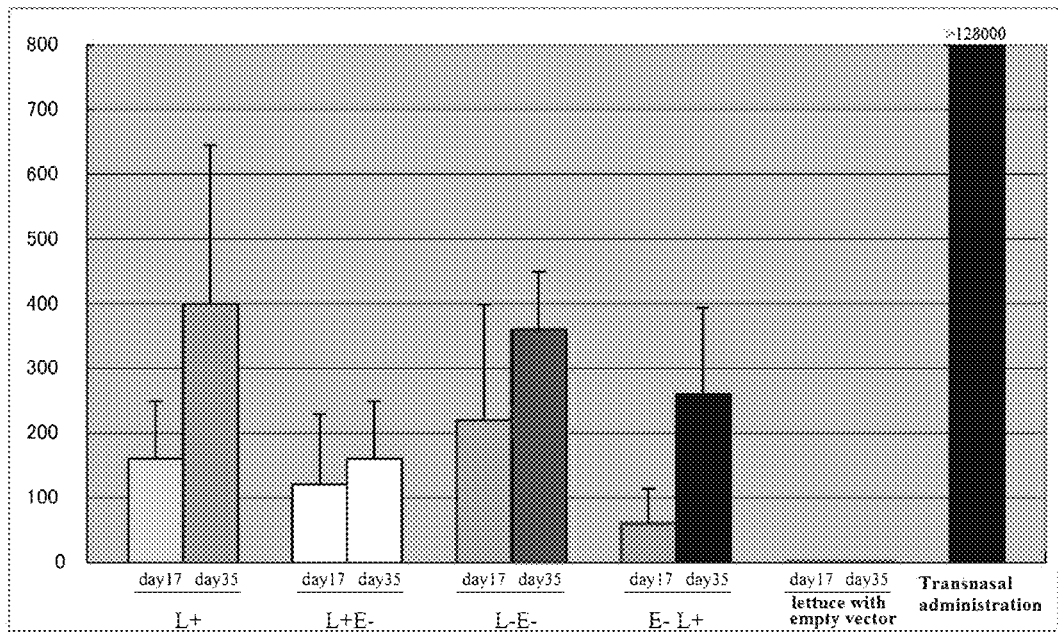
FIG. 5 is a graph illustrating the anti-IgA antibody titer in the serum of the mice orally administered with the transformed plants.
Figure 6:
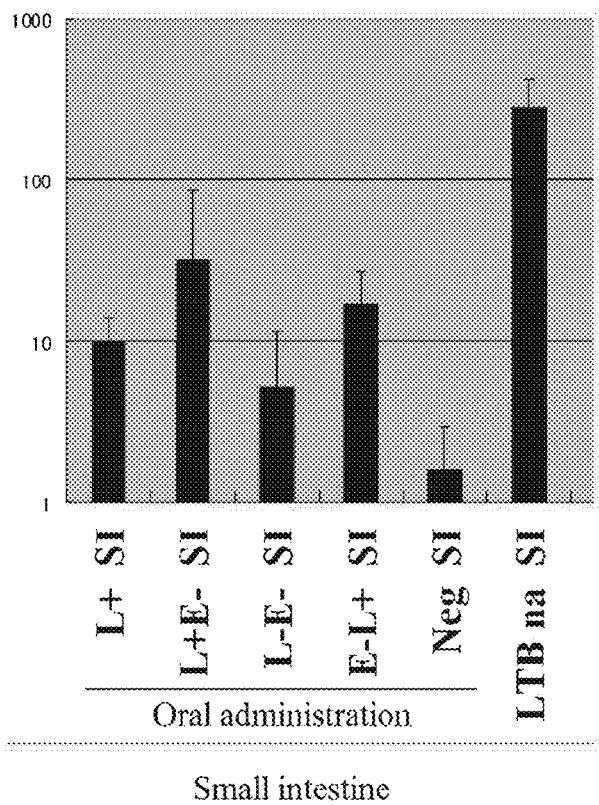
FIG. 6 is a graph illustrating the anti-IgA antibody titer in the intestinal lavage solution of the mice orally administered with the transformed plants.

The agent for controlling colibacillosis according to the present invention comprises as an effective ingredient a fusion protein containing a subunit of Shiga toxin and a subunit of *Escherichia coli* heat-labile toxin.
Shiga toxin (Stx) is a proteinaceous toxin produced by enterohemorrhagic *Escherichia coli* (EHEC, STEC), and classified into type 1 (Stx1) and type 2 (Stx2). Stx1 is further classified into subclasses a to d, and Stx2 is further classified into subclasses a to g. Shiga toxin is a holotoxin composed of one A subunit molecule which is the main body of the toxin, and five B subunit molecules responsible for binding to the intestinal mucosa. The toxin has a function of inhibiting protein synthesis by acting on ribosomes in eukaryotic cells. Shiga toxin is a virulence factor which directly causes various types of pathological conditions such as hemorrhagic diarrhea, hemolytic-uremic syndrome (HUS), and acute encephalopathy that are observed upon infection with enterohemorrhagic *Escherichia coli* or *Shigella*. Shiga toxin is also referred to as a verotoxin, since it exhibits cell toxicity to cultured cells (Vero cells) derived from the renal epithelium of African green monkey.

Edema disease of swine is caused by oral infection with enterohemorrhagic *Escherichia coli* which produces Stx2e, and the toxin produced thereby in the small intestine is absorbed into the body. After the infection, systemic edema is observed, and the disease progresses rapidly to result in high mortality.

In the present specification, the A subunit of Stx2e (Stx2eA) is represented by the amino acid sequence of SEQ ID NO: 6, and the B subunit of Stx2e (Stx2eB) is represented by the amino acid sequence of SEQ ID NO: 8. The SEQ ID NO: 8 represents the amino acid sequence of a mature region (excluding a secretory signal peptide to periplasm, Ala19 to Asn87) of the Stx2e B subunit protein (GenBank Accession No. AAQ63639). As used herein, when simply referred to as "Stx2e B subunit protein" or "Stx2eB", it refers to a Stx2e B subunit protein having the above described amino acid sequence of the mature region.

In the present invention, Asn73 in the Stx2e B subunit (in other words, Asn residue at position 55 in the amino acid sequence of SEQ ID NO: 8) is replaced with Ser, for example. The amino acid sequence in which the Asn residue at position 55 of SEQ ID NO: 8 is replaced with Ser (Asn73Ser) is represented by SEQ ID NO: 10.

Stx2eA and Stx2eB may have the amino acid sequences represented by SEQ ID NO: 6, and SEQ ID NO: 8 or 10, respectively, except that one or several amino acids are substituted, deleted, inserted and/or added, as long as they are capable of eliciting an immune response when administered to a pig. The term "several" as used above means, for example, preferably a number of from 2 to 30, more preferably from 2 to 20, and still more preferably from 2 to 10 in Stx2eA; and a number of preferably from 2 to 10, more preferably from 2 to 5, and still more preferably from 2 to 3 in Stx2eB.

Further, Stx2eA and Stx2eB may be proteins having a sequence identity of preferably 85% or more, more preferably 90% or more, and still more preferably 95% or more to the amino acid sequences represented by SEQ ID NO: 6, and SEQ ID NO: 8 or 10, respectively, and capable of eliciting an immune response when administered to a pig.

However, in the amino acid sequence represented by SEQ ID NO: 10 except for including the above mentioned substitution and/or the like, or in the amino acid sequence having the above mentioned identity to the sequence of SEQ ID NO: 10, the residue at position 55 remains replaced with Ser.

The Stx2e to be used in the present invention may be either the A subunit or the B subunit, but the B subunit is preferred.

*Escherichia coli* diarrhea is caused by proteinaceous *Escherichia coli* heat-labile toxin (LT) produced by enterotoxigenic *Escherichia coli* (ETEC). LT is a holotoxin composed of one A subunit molecule which is the main body of the toxin and five B subunit molecules. The A subunit of LT (LTA) enters into a cytoplasm, and increases the concentration of intracellular cAMP to activate plasma membrane chloride channels, thereby causing a leakage of water into the intestinal tract, in other words, inducing a state of diarrhea. The B subunit of LT (LTB) is nontoxic, and involved in the adhesion of the LT toxin to intestinal tract cells.

Examples of LTB include a protein having the amino acid sequence represented by SEQ ID NO: 12. However, LTB may be any protein having the amino acid sequence represented by SEQ ID NO: 12 except that one or several amino acids are substituted, deleted, inserted and/or added, as long as it is capable of eliciting an immune response when administered to a pig. The term "several" as used above means, for example in LTB, a number of preferably from 2 to 10, more preferably from 2 to 5, and still more preferably from 2 to 3. The amino acid sequence represented by SEQ ID NO: 12 has been registered in Gen Bank under the Accession No. AAL55672.

Further, LTB may be a protein having a sequence identity of preferably 85% or more, more preferably 90% or more, and still more preferably 95% or more to the amino acid sequence represented by SEQ ID NO: 12, and capable of eliciting an immune response when administered to a pig.

In a preferred embodiment of the present invention, a sugar chain is added to the B subunit of *Escherichia coli* heat-labile toxin. More preferably, an N-linked sugar chain is added to Asn residue at position 90 in the B subunit of *Escherichia coli* heat-labile toxin (in other words, position 90 in the amino acid sequence of SEQ ID NO: 8). In the description regarding the LTB subunit protein in which position 90 in its amino acid sequence is an Asn residue, the term "several" means that, preferably from 2 to 10, more preferably from 2 to 5, and still more preferably from 2 to 3 amino acids may be substituted, deleted, inserted and/or added in the amino acid sequence represented by SEQ ID NO: 12, at positions other than the position 90 at which the Asn residue resides.

Further, the LTB subunit protein in which position 90 in its amino acid sequence is an Asn residue, may be a protein having a sequence identity of preferably 85% or more, more preferably 90% or more, and still more preferably 95% or more to the amino acid sequence represented by SEQ ID NO: 12, other than having an Asn residue at position 90 in the amino acid sequence represented by SEQ ID NO: 12.

The amino acid sequence of the LTB subunit protein, which is the same as the amino acid sequence of SEQ ID NO: 8 except that the residue at position 90 is replaced with a Ser residue, is represented by SEQ ID NO: 14. The LTB subunit protein may have an amino acid sequence represented by SEQ ID NO: 14 except for including the above mentioned substitution and/or the like, or an amino acid sequence having the above mentioned identity to the sequence of SEQ ID NO: 14. However, in the amino acid sequence represented by SEQ ID NO: 14 except for including the above mentioned substitution and/or the like, or in the amino acid sequence having the above mentioned identity to the sequence of SEQ ID NO: 14, the residue at position 90 remains replaced with Ser.

Since the agent for controlling colibacillosis according to the present invention comprises as an effective ingredient the fusion protein containing Shiga toxin and *Escherichia coli* heat-labile toxin, as described above, it is capable of functioning as a vaccine or an immunostimulant which induces, preferably, antibodies against *Escherichia coli* heat-labile toxin, such as IgA and IgG.

In a preferred embodiment of the present invention, antibodies induced by the agent for controlling colibacillosis according to the present invention have a neutralizing activity against heat-labile enterotoxin (LTp).

The agent for controlling colibacillosis according to the present invention has an effect of controlling the symptoms of colibacillosis (vaccine effect, immunostimulating effect, or therapeutic effect). Colibacillosis as used in the present invention includes edema disease of swine (enterotoxigenic *Escherichia coli*), *Escherichia coli* diarrhea (enterohemorrhagic *Escherichia coli*), enteroinvasive *Escherichia coli*, enteroaggregative *Escherichia coli*, and enteropathogenic *Escherichia coli*.

The fusion protein which is the effective ingredient of the agent for controlling colibacillosis according to the present invention is a protein produced by a genetic engineering technique, such that two or more protein genes (protein coding regions) are liked to be transcribed and translated continuously, thereby producing one protein. In the fusion protein to be used in the present invention, proteins may be directly fused to each other, or proteins may be bound via a peptide linker.

In a preferred embodiment, the agent for controlling colibacillosis according to the present invention is a fusion protein in which a B subunit of Shiga toxin protein and the B subunit of *Escherichia coli* heat-labile toxin are tandemly linked via a peptide linker.

In the present invention, the arrangement order in which the B subunit of Shiga toxin protein and the B subunit of *Escherichia coli* heat-labile toxin are fused may be arbitrary, and either one may be arranged on the side of the N-terminus. However, when a recombinant protein is expressed in plants, the accumulation of the protein tends to be higher when Stx2eB is arranged on the side of the N-terminus.

In the present specification, the term "agent for controlling colibacillosis" may be used to generally refer to: the agent for controlling colibacillosis comprising as an effective ingredient the fusion protein containing the subunit of Shiga toxin and the subunit of *Escherichia coli* heat-labile toxin; the fusion protein in which the B subunit of Shiga toxin protein and the B subunit of *Escherichia coli* heat-labile toxin are tandemly linked via a peptide linker; a DNA construct coding for the fusion protein; a plant transformed with a vector containing the DNA construct coding for the fusion protein; and the like. The agent for controlling colibacillosis according to the present invention may be in the form of a pharmaceutical such as a vaccine or an immunostimulant, or in the form of a feed, as long as it includes the above mentioned fusion protein. In the present invention, the term "controlling" includes both prevention and treatment.

The peptide linker to be used in the present invention preferably has from 12 to 25, and more preferably from 12 to 22 amino acids. Further, the peptide linker to be used in the present invention preferably has a proline content of from 20 to 27%, and more preferably, from 20 to 25%.

Prolines are preferably arranged with an interval of two or three amino acids in the peptide linker. However, even in the above mentioned arrangement, five or less, preferably four or less amino acids other than proline may be arranged at the terminus of the peptide. Such a preferred peptide linker is disclosed, for example, in WO 2009/133882 A.

In the present invention, the peptide linker is preferably a peptide (PG12) having the amino acid sequence as represented by SEQ ID NO: 2, or a peptide (PG12v2) having the amino acid sequence represented by SEQ ID NO: 4. Alternatively, the peptide linker may be a peptide having a sequence identity of 90% or more, preferably 95% or more, to these sequences.

In the fusion protein to be used in the present invention, it is preferred that the B subunit of Shiga toxin and the B subunit of *Escherichia coli* heat-labile toxin be tandemly linked via the peptide. In the fusion protein to be used in the present invention, it is more preferred that each of the B subunits be tandemly linked via PG12 (SEQ ID NO: 2) or PG12v2 (SEQ ID NO: 4). The fusion protein to be used in the present invention may include an A subunit, and when it does, it is preferred that the A subunit be detoxified.

Further, it is preferred that the above mentioned peptide linker be further added to the C terminus of the fusion protein to be used in the present invention. In particular, it is preferred that PG12 or PG12v2 be added to the C terminus of the fusion protein to be used in the present invention.

The fusion protein to be used in the present invention has, for example, any one of the amino acid sequences represented by SEQ ID NOs: 15 to 18. In the fusion protein having any one of the amino acid sequences represented by SEQ ID NOs: 15 to 18, the B subunit of Shiga toxin and the B subunit of *Escherichia coli* heat-labile toxin are tandemly linked via PG12 or PG12v2, and another PG12 or PG12v2 is further added to its C terminus.

By using a peptide such as the PG12 or PG12v2 as a linker for linking the subunit proteins in the above mentioned fusion protein, the level of the fusion protein accumulated in plant cells will be increased.

In the fusion protein to be used in the present invention, a secretory signal peptide derived from a plant or a chloroplast transit signal peptide is preferably added to its amino terminus. The term "added" as used herein is a concept including both the case where the secretory signal peptide is directly bound to the amino terminus of the fusion protein in which the subunit proteins are linked via the above mentioned peptide, and the case where the secretory signal peptide is bound thereto via another peptide.

The secretory signal peptide is preferably derived from a plant belonging to the family Solanaceae, Brassicaceae, or Asteraceae, more preferably, derived from a plant belonging to the genus *Nicotiana*, *Arabidopsis*, *Lactuca* or the like, and still more preferably derived from tobacco (*Nicotiana tabacum*), *Arabidopsis thaliana*, lettuce (*Lactuca sativa*) or the like.

Further, the secretory signal peptide is preferably derived from β-D-glucan exohydrolase of *Nicotiana tabacum* or 38k-Da peroxidase of *Nicotiana tabacum* (GenBank Accession D 42064). The secretory signal peptide may be, for example, a peptide derived from the β-D-glucan exohydrolase of *Nicotiana tabacum* and having the amino acid sequence represented by SEQ ID NO: 28. The nucleotide sequence of a DNA which codes for the β-D-glucan exohydrolase of *Nicotiana tabacum* is represented, for example, by the sequence of SEQ ID NO: 27.

Preferred chloroplast transit signal peptides are described, for example, in WO 2009/004842 A and WO 2009/133882 A.

In the fusion protein to be used in the present invention, a signal peptide such as an endoplasmic reticulum retention signal peptide or a vacuolar transport signal peptide may be added to its carboxyl terminus. The term "added" as used herein is a concept including both the case where the signal peptide is directly bound to the carboxyl terminus of the fusion protein, and the case where the signal peptide is bound thereto via another peptide. In the present specification, a hybrid protein in which the secretory signal peptide is added to its amino terminus and the endoplasmic reticulum retention signal peptide is added to the carboxyl terminus is also referred to as an endoplasmic reticulum-type (ER) hybrid protein, and a DNA construct coding for the endoplasmic reticulum-type fusion protein is referred to as an endoplasmic reticulum-type DNA construct. Many studies have reported that the endoplasmic reticulum-type fusion protein is efficiently accumulated in eukaryotes.

In the fusion protein to be used in the present invention, it is preferred that the endoplasmic reticulum retention signal peptide be added to its carboxyl terminus. Preferred endoplasmic reticulum retention signal peptides are disclosed, for example, in WO 2009/004842 A and WO 2009/133882 A. Among these, HDEL sequence (SEQ ID NO: 29) can be used.

Other preferred vacuolar transport signal peptides are disclosed, for example in WO 2009/004842 A and WO 2009/133882 A.

The fusion protein to be used in the present invention can be synthesized chemically, or may be produced by genetic engineering. A method for producing the fusion protein by genetic engineering will be described later.

The DNA construct to be used in the present invention is characterized by containing a DNA coding for the fusion protein according to the present invention.

In other words, the DNA construct to be used in the present invention includes a DNA in which a DNA coding for the subunit of Shiga toxin and a DNA coding for the subunit of *Escherichia coli* heat-labile toxin, preferably, a DNA coding for the B subunit of Shiga toxin and a DNA coding for the B subunit of *Escherichia coli* heat-labile toxin, are tandemly linked via a DNA coding for the peptide. The DNA coding for the peptide linker is represented, for example, by SEQ ID NO: 1 (PG12) or SEQ ID NO: 3 (PG12v2). Examples of the DNA coding for the Shiga toxin protein include a DNA (SEQ ID NO: 5) coding for Stx2eA, a DNA (SEQ ID NO: 7) coding for Stx2eB (Asn73), and a DNA (SEQ ID NO: 9) coding for Stx2eB (Asn73Ser). Examples of the DNA coding for the *Escherichia coli* heat-labile toxin include a DNA (SEQ ID NO: 11) coding for the B subunit (Asn90) and a DNA (SEQ ID NO: 13) coding for the B subunit (Asn90Ser). The DNA coding for the peptide, the DNA coding for the Shiga toxin protein, and the DNA coding for the *Escherichia coli* heat-labile toxin are linked in-frame, excluding stop codons.

The DNA coding for the Shiga toxin protein and the DNA coding for the *Escherichia coli* heat-labile toxin can be obtained by a common genetic engineering technique based, for example, on the nucleotide sequences of SEQ ID NO: 9 and SEQ ID NO: 11 or 13, respectively. Specifically, a cDNA library is prepared from a bacterium which produces each Shiga toxin according to a conventional method, and a desired clone is selected from the library using a probe prepared based on the above mentioned nucleotide sequence. Alternatively, each of the DNAs can also be synthesized chemically, based on the above mentioned nucleotide sequence, or synthesized by PCR using genomic DNA as a template, and 5'- and 3'-terminal nucleotide sequences of the above mentioned sequence as primers.

The DNA coding for the fusion protein to be used in the present invention is represented, for example, by any one of the sequences represented by SEQ ID NOs: 19 to 22.

In the DNA coding for the fusion protein, it is also preferred that a codon(s) corresponding to an amino acid(s) constituting the fusion protein be modified as appropriate such that the amount of the translated hybrid protein is increased depending on the host cell in which the fusion protein is produced.

The modification of the codon(s) can be carried out, for example, by referring to a method disclosed by Kang et al., (2004). Further, examples of the modification method include a method for selecting a codon(s) frequently used in the host cell, a method for selecting a codon(s) having a high GC content, and a method for selecting a codon(s) frequently used in housekeeping genes in the host cell.

The DNA coding for the fusion protein may also be a DNA which hybridizes with the DNA having any one of the nucleotide sequences of SEQ ID NOs: 19 to 22 under stringent conditions. The term "stringent conditions" refers to the conditions in which a so-called specific hybrid is formed, but a non-specific hybrid is formed. Examples of the stringent conditions include those in which two DNAs having a high sequence identity to one another, preferably two DNAs having a sequence identity of 80% or more, more preferably 90% or more, and particularly preferably 95% or more to one another are hybridized with each other, but two DNAs having a sequence identity lower than that described above are not hybridized. The conditions maybe, for example: 2×SSC (300 mM NaCl, 30 mM citric acid) at 42° C.; and preferably: 0.1×SSC (15 mM NaCl, 1.5 mM citric acid) at 60° C.

In the DNA construct to be used in the present invention, it is preferred that the DNA coding for the above mentioned fusion protein be operably-linked to an enhancer. The term "operably" as used herein means that, when the DNA construct to be used in the present invention is inserted into a vector including a suitable promoter, and the vector is introduced into a suitable host cell, the fusion protein is produced in the host cell. Further, the term "linked" refers to both the case in which two DNAs are directly linked and the case in which two DNAs are linked via another nucleotide sequence.

Examples of the enhancer include Kozak sequence and a 5'-untranslated region of an alcohol dehydrogenase gene derived from a plant. Particularly preferably, the DNA coding for the hybrid protein is operably-linked to the 5'-untranslated region of an alcohol dehydrogenase gene derived from a plant.

The 5'-untranslated region of an alcohol dehydrogenase gene refers to a region including a nucleotide sequence from the transcription start site before the translation start site (ATG, methionine), of a gene coding for the alcohol dehydrogenase. This region has a function to increase the translation level. The phrase "function to increase the translation level" refers to a function to increase the amount of a protein produced by translation when the information encoded in a structural gene is transcribed and then translated to produce a protein. The above mentioned region may be a region derived from a plant. However, it is preferably derived from a plant belonging to the family Solanaceae, Brassicaceae, or Asteraceae, more preferably, derived from a plant belonging to the genus *Nicotiana, Arabidopsis, Lactuca* or the like, and still more preferably derived from tobacco (*Nicotiana tabacum*), *Arabidopsis thaliana*, lettuce (*Lactuca sativa*) or the like.

The 5'-untranslated region of an alcohol dehydrogenase gene may be, for example, the 5'-untranslated region of an alcohol dehydrogenase gene (NtADH 5'UTR) (SEQ ID NO: 30) derived from tobacco (*Nicotiana tabacum*). In particular, a higher translation can be expected by using the NtADH 5'UTR region in which three nucleotides upstream of the translation start site are modified (NtADHmod 5'UTR) (SEQ ID NO: 31).

Methods for obtaining the 5'-untranslated region of an alcohol dehydrogenase gene derived from a plant are described, for example, in JP 2012-19719 A and WO 2009/133882 A.

In the nucleotide sequence of the NtADHmod 5'UTR such as one represented by SEQ ID NO: 31, one or several nucleotides may be substituted, deleted, inserted and/or added, as long as its function to increase the translation level is maintained. The term "several" as used above means preferably a number of from 2 to 10, more preferably from 2 to 5, and particularly preferably from 2 to 3.

Further, a DNA having a sequence identity of preferably 85% or more, and particularly preferably 90% or more to the NtADHmod 5'UTR and having a function to increase the translation level may also be used.

It is possible to determine whether the above mentioned region has an intended function to increase the translation level or not, for example, by a transient assay using a GUS (β-glucuronidase) gene or luciferase gene as a reporter gene in tobacco cultured cells, or an assay in transformed cells engineered to carry those genes in a chromosome.

The DNA construct to be used in the present invention has, for example, the nucleotide sequence represented by any one of SEQ ID NOs: 23 to 26.

The DNA construct having the nucleotide sequence represented by SEQ ID NO: 23 (L+E−) is a DNA construct comprising the DNA coding for the fusion protein in which one LTB protein (wild type Asn90) and one Stx2eB protein (mutant type Asn73Ser) are tandemly linked via PG12, the secretory signal peptide is added to its amino terminus, and the endoplasmic reticulum retention signal peptide is added to its carboxyl terminus, linked to the NtADHmod 5'UTR (SEQ ID NO: 31).

The DNA construct having the nucleotide sequence represented by SEQ ID NO: 24 (L−E−) is a DNA construct comprising the DNA coding for the fusion protein in which one LTB protein (mutant type Asn90Ser) and one Stx2eB protein (mutant type Asn73Ser) are tandemly linked via PG12, the secretory signal peptide is added to its amino terminus, and the endoplasmic reticulum retention signal peptide is added to its carboxyl terminus, linked to the NtADHmod 5'UTR (SEQ ID NO: 31).

The DNA construct having the nucleotide sequence represented by SEQ ID NO: 25 (E−L+) is a DNA construct comprising the DNA coding for the fusion protein in which one Stx2eB protein (mutant type Asn73Ser) and one LTB protein (wild type Asp90) are tandemly linked via PG12v2, the secretory signal peptide is added to its amino terminus, and the endoplasmic reticulum retention signal peptide is added to its carboxyl terminus, linked to the NtADHmod 5'UTR (SEQ ID NO: 31).

The DNA construct having the nucleotide sequence represented by SEQ ID NO: 26 (E−L−) is a DNA construct comprising the DNA coding for the fusion protein in which one Stx2eB protein (mutant type Asn73Ser) and one LTB protein (mutant type Asp90Ser) are tandemly linked via PG12v2, the secretory signal peptide is added to its amino terminus, and the endoplasmic reticulum retention signal peptide is added to its carboxyl terminus, linked to the NtADHmod 5'UTR (SEQ ID NO: 31).

The DNA construct to be used in the present invention can be prepared by a common genetic engineering technique, which includes the following procedures: digesting each of the DNAs such as the 5'-untranslated region of an alcohol dehydrogenase gene derived from a plant, a DNA coding for the secretory signal peptide derived from a plant, the DNA coding for the fusion protein, and a DNA coding for the endoplasmic reticulum retention signal peptide with a suitable restriction enzyme; and ligating the resulting fragments with a suitable ligase.

The recombinant vector to be used in the present invention is characterized by comprising the above mentioned DNA construct. The recombinant vector to be used in the present invention may be any vector in which the DNA coding for the fusion protein is inserted into the vector such that the DNA can be expressed in a host cell into which the vector is introduced. The vector is not particularly limited as long as it can be replicated in a host cell, and examples thereof include a plasmid DNA, a viral DNA and the like. Further, the vector preferably includes a selection marker such as a drug resistance gene. The plasmid DNA can be prepared from *Escherichia coli* or *Agrobacterium tumefaciens* by the alkaline extraction method (Birnboim, H. C. & Doly, J. (1979) Nucleic acid Res 7: 1513) or a variation thereof. Commercially available plasmids such as pBI221, pBI121, pBI101, pIG121Hm and the like can also be used. The viral DNA may be, for example, pTB2 (see, Donson J., Kerney C M., Hilf M E., Dawson W O. Systemic expression of a bacterial gene by a tobacco mosaic virus-based vector. Proc. Natl. Acad. Sci. (1991) 88: 7204-7208).

A promoter to be used in the vector can be selected as appropriate depending on the type of host cell into which the vector is introduced. Preferred examples of the promoter include a cauliflower mosaic virus 35S promoter (Odell et al. 1985 Nature 313:810), a rice actin promoter (Zhang et al. 1991 Plant Cell 3:1155), a corn ubiquitin promoter (Cornejo et al. 1993 Plant Mol. Biol. 23:567) and the like. Further, a terminator to be used in the vector may also be selected as appropriate depending on the type of host cell into which the vector is introduced. Preferred examples of the terminator include a nopaline synthase gene transcription terminator, a cauliflower mosaic virus 35S terminator, *Arabidopsis thaliana* heat shock protein 18.2 gene terminator (HSP-T) and the like. A preferred terminator to be used in the present invention is, for example, HSP-T represented by SEQ ID NO: 32.

The recombinant vector to be used in the present invention can be prepared, for example as follows.

First, the above mentioned DNA construct is digested with a suitable restriction enzyme, or a restriction enzyme site is added to the DNA construct by PCR. Subsequently, the resulting DNA construct is inserted into the restriction enzyme site or multicloning site of a vector.

The transformant to be used in the present invention is characterized by being transformed with the above mentioned recombinant vector. The host cells to be used for the transformation may be eukaryotic cells or prokaryotic cells.

The eukaryotic cells are preferably plant cells, and among these, particularly preferred are cells of plants belonging to the family Asteraceae (including those belonging to the genus *Lactuca*, for example), Solanaceae, Brassicaceae, and Chenopodiaceae. Further, the eukaryotic cells are preferably cells of plants belonging to the genus *Lactuca*, particularly preferably lettuce (*Lactuca sativa*) cells. When the lettuce cells are used as the host cells, a cauliflower mosaic virus 35S RNA promoter or the like can be used in the vector.

The prokaryotic cells may be cells of *Escherichia coli, Agrobacterium tumefaciens* or the like.

The transformant to be used in the present invention can be prepared by introducing the vector to be used in the present invention into host cells using a common genetic engineering technique. Examples of the method which can be used to introduce the vector include: a method using *Agrobacterium* (Hood, et al., 1993, Transgenic, Res. 2:218, Hiei, et al., 1994 Plant J. 6:271), an electroporation method (Tada, et al., 1990, Theor. Appl. Genet, 80:475), a polyethylene glycol method (Lazzeri, et al., 1991, Theor. Appl. Genet. 81:437), a particle gun method (Sanford, et al., 1987, J. Part. Sci. tech. 5:27) a polycation method (Ohtsuki), and the like.

After introducing the vector to be used in the present invention into the host cells, the above mentioned transformant can be selected based on the phenotype of the selective marker. By culturing the selected transformant, the Shiga toxin protein can be produced. The culture medium and conditions to be used in the culture can be selected as appropriate, depending on the type of the transformant.

When plant cells are used as the host cells, culture of selected plant cells in accordance with a conventional method allows for regeneration of a plant body, and for accumulation of the Shiga toxin protein inside the plant cells or outside the cell membrane of the plant cells. The method varies depending on the type of plant cells to be used, and examples thereof include the method of Visser et al. (Theor. Appl. Genet 78:594 (1989)) for potato cells, and the method of Nagata and Takebe (Planta 99:12 (1971)) for tobacco cells.

In the case of lettuce (*Lactuca sativa*) for example, the regeneration of a shoot is possible in MS culture medium containing 0.1 mg/l of NAA (naphthaleneacetic acid), 0.05 mg/l of BA (benzyladenine) and 0.5 g/l of polyvinylpyrrolidone, and the rooting of the regenerated shoot can be achieved by culturing it in ½ MS culture medium containing 0.5 g/l of polyvinylpyrrolidone.

Further, the seed to be used in the present invention can be collected from the thus regenerated plant body. When the seed to be used in the present invention is seeded and grown by an appropriate method, a plant body capable of producing the bacterial toxin protein can be obtained, and the thus obtained plant body is also included in the above mentioned transformant.

*Agrobacterium tumefaciens* infects a plant through a wound in the plant, and carries a large extrachromosomal element referred to as a Ti (tumor-inducing) plasmid. Many laboratories have devoted considerable effort over several years to develop an *Agrobacterium* system, and as a result, it has become possible to transform various types of plant tissues as desired. Representative plants transformed by the above mentioned technique include tobacco, tomato, sunflower, cotton, rapeseed, potato, poplar, soybean, strawberry, rice, and the like.

It has been demonstrated that various types of plants can be regenerated from tissues transformed with *Agrobacterium tumefaciens*. Examples of such plants include sunflower, tomato, white clover, rapeseed, cotton, tobacco, potato, corn, strawberry, rice, and many other kinds of vegetable crops.

In the present invention, it is preferred that an edible plant such as lettuce, as described above, be transformed with an *Agrobacterium* Ti vector.

The agent for controlling colibacillosis according to the present invention may include the above mentioned transformant. The agent for controlling colibacillosis according to the present invention may include the entire or a part of the transformant including the above mentioned fusion protein. Further, the transformant can be used as it is, or it can be dried, crushed, and/or the like before being used. It is also possible to add an adjuvant which enhances the immunogenicity of the fusion protein to the agent for controlling colibacillosis according to the present invention. In general, aluminum hydroxide, cholera toxin (CTB), heat-labile enterotoxin (LTB) or a bacterial flagellum such as salmonella flagellin is used as an adjuvant.

The method for controlling colibacillosis according to the present invention is characterized by administering a plant body transformed with the above mentioned DNA construct, or a dried product or a ground product thereof, to an animal. A preferred subject to be administered with the agent for controlling colibacillosis according to the present invention may be, for example, a pig, cow, chicken, sheep, goat, dog, cat or the like, but it is preferably a pig. The immunization by the agent for controlling colibacillosis according to the present invention is carried out on a young pig in the lactation period or of up to 120-day old, preferably on a young pig in the lactation period or of up to 90-day old. Further, the immunization is preferably carried out on a mother pig during, before and after the reproductive period. Examples of the method for carrying out the immunization include a method in which a plant body transformed with the DNA construct is administered to a mother pig, and milk containing antibodies produced by the mother pig is fed to a young pig; a method in which a plant body transformed with the DNA construct is administered to a young pig in the lactation period or of up to 90-day old to directly immunize the young pig; and the like.

Examples of the method for administering the agent for controlling colibacillosis according to the present invention to a pig include a method in which a plant body transformed with the DNA construct, or a dried product or a ground product thereof, is mixed with a feed to be fed to a pig; a method in which the agent is administered to a pig by nasal drops; and the like. It is preferred that the agent for controlling colibacillosis according to the present invention be administered for a plurality of times at certain intervals. For example, the agent may be administered every four to seven days for a total of two to three times.

Examples of the present invention will now be described. However, the present invention is not limited by the following Examples.

EXAMPLES

Example 1. Construction of Protein Genes for Expression in *Escherichia coli*

As candidate protein antigens, 1) a nontoxic B subunit of heat-labile toxin (LTB) produced by toxigenic *Escherichia coli*; and 2) a nontoxic B subunit of verotoxin (Stx2eB) produced by enterohemorrhagic *Escherichia coli* were used.

When LTB is produced in the endoplasmic reticulum of lettuce (*Lactuca sativa*), an N-linked sugar chain is added to Asn residue at position 90 in the resulting LTB. However, a mutant in which the Asn residue was replaced with Ser (hereinafter, a wild type is denoted as L+, and a mutant type is denoted as L−) was also prepared. A glycosylation site mutant (Asn73Ser, hereinafter, denoted as E−) of Stx2eB was used as the Stx2eB, and linked with L+ or L− in two different arrangement orders of fusion, to prepare four types of fusion antigens (L+E−, L−E−, E−L+ and E−L−). The nucleotide sequences of the resulting fragments (L+E−, L−E−, E−L+ and E−L−) are shown as SEQ ID NOs: 19 to 22, respectively. Each of the antigens was fused with the signal peptide of the Stx2eB, and linked to an IPTG-inducible promoter, and inserted into a pET101 vector (Invitrogen) (FIG. 1).

Specifically, a region containing a ribosome binding site (SD sequence) and the signal peptide of the Stx2eB was amplified using a Stx2eB-SDSP-F primer (aaa<u>tctaga</u>aataataaggagttaagaatgaagaa (SEQ ID NO: 33), the underline indicates the XbaI site) and a Stx2eB-SP-R primer (aaa<u>ggatcc</u>tgcattaacagaaaccaatgcaaa (SEQ ID NO: 34), the underline indicates the BamHI site).

The resulting fragment was treated with XbaI and BamHI and inserted into the XbaI-BamHI of pRI909 L+, L−, L+E−, L−E−, E−L+ and E−L−, shown below. A SD sequence-Stx2eBSP-antigenic region-HDEL fragment was cleaved out from each of the pRI909 plasmids using XbaI and SacI, and each fragment was inserted into the XbaI-SacI gap of the pET101 (Invitrogen) (FIG. 1).

Example 2. Production of Antigen Using *Escherichia coli*

Each of the expression vectors were introduced into *Escherichia coli* (BL21 DE3) for producing a recombinant protein. A single colony of the resulting recombinant *Escherichia coli* was selected, and cultured overnight in a LB medium (LB+Amp medium) containing 100 mg/L of ampicillin, followed by mixing with an equal amount of 50% glycerol, and the resultant was stocked at a temperature of −80° C.

The bacteria were collected by scraping the glycerol stock with a tip, seeded in a LB+Amp medium, and cultured overnight at 37° C. and at 180 rpm. One ml of the resulting culture liquid was subcultured to a 2 L flask with a baffle containing 250 ml of LB+Amp culture medium, and the resultant was cultured at 37° C. and at 180 rpm. At the timing when the value of O. D. was at 0.4 to 0.6, IPTG (final concentration, 1 mM) was added, followed by culturing at 25° C. and at 120 rpm, for four hours. The culture liquid was transferred to a 50 ml centrifuge tube, and the resultant was centrifuged at 8,000 rpm at room temperature for five minutes, to collect bacterial cells. Then the culture medium was removed, and 50 ml of culture liquid was further added to the centrifuge tube, followed by centrifugation at 8,000 rpm, at room temperature for five minutes. The collected bacterial cells were stored at −80° C.

Example 3. Preparation of Soluble Protein from *Escherichia coli* Expressing Recombinant LTB To the bacterial cells obtained in Example 2, a lysis buffer (BugBuster (Merck Millipore); PBS containing 0.2 mg/ml of lysozyme, 1 mM of PMSF, 30 U/ml of DNase; pH 7.4) was added in an amount of 20 ml per 125 ml of the culture liquid, and stirred on a rotator at room temperature for 30 minutes. Then the centrifugation was performed at 8,000 rpm and 4° C. for 20 minutes, and the resulting supernatant was collected and transferred to a new centrifuge tube. The same centrifugation operation was repeated two more times.

Example 4. Purification of Recombinant Antigen Using Galactose Column

A quantity of 5 ml of galactose beads (Immobilized D-Galactose Gel, No. 20372; Thermo Fisher Scientific, Inc.) equilibrated with PBST (PBS containing 0.05% Tween-20; pH 7.4) was added to the solution of the lysed bacterial cells obtained in Example 3, and the resultant was stirred on a rotator for two hours. The suspension was loaded on a column for chromatography (Econo-Pac chromatography column, BIO-RAD laboratories, Inc., #732-1010), and the eluted solution was discarded. A quantity of 120 ml of PBST was added to the column to wash the column. The absorbance at 280 nm of the solution dripping from the column was measured using a nano-drop spectrophotometer, and it was confirmed that the O. D. was at baseline. When washing was insufficient, PBST was added as appropriate to wash the column. PBST containing 0.5 M galactose was added in an amount of 1 ml per 1 fraction, to elute LTB. After confirming that no more protein was being eluted, by measuring the absorbance at 280 nm, 50 ml of 6 M guanidine hydrochloric acid was added to wash the column. The remaining guanidine hydrochloric acid was replaced with 20% ethanol, and the column was stored at 4° C.

Example 5. Evaluation of Immunogenicity of Purified Antigen

The results of an affinity purification, performed utilizing the affinity of LTB to galactose, are shown in FIG. 2A. Further, 0.5 M galactose was used to carry out a competitive elution, and the resulting antigen was used for immunizing small animals.

When SDS-PAGE was carried out under conditions without thermal denaturation, the purified LTB was detected at a position of about 70 kDa (FIG. 2B), suggesting the formation of pentamers. Purified antigens of L− and L+E− were prepared in the same manner as described above. Since E−L+ was insolubilized in *Escherichia coli*, the purification of E−L+ antigen was not carried out.

Example 6. Confirmation of Immunogenicity Using Rabbits

The purified antigens prepared in Examples 4 and 5 were used to immunize rabbits by injection, and the measurement of the antibody titer was carried out. An increase in anti-LTp antibody titer was observed in all the rabbits immunized with any of the L+, L− and L+E− antigens. The neutralizing activity against LTp toxin was also observed (Table 1). It can be seen from the result shown in Table 1 that: (1) the introduction of a mutation to the glycosylation site of LTB does not have an impact on the induction of neutralizing antibodies; and (2) the agent for controlling colibacillosis according to the present invention is capable of inducing a LTp neutralizing antibody. On the other hand, an increase in anti-Stx2e antibody titter was small, and the neutralizing activity against Stx2e toxin was not observed.

TABLE 1

| Immunogen | IgG antibody titer | | Neutralizing activity |
|---|---|---|---|
| | anti-LTp | anti-Stx2e | LTp[1)] |
| L+ #1 | 2048000 | 200 | 0.1250 |
| L+ #2 | 1024000 | 100 | 0.1250 |
| L− #1 | 4096000 | <100 | 0.1250 |
| L− #2 | 2048000 | 200 | 0.0625 |
| L+E− #1 | 1024000 | 800 | 0.2500 |
| L+E− #2 | 256000 | 1600 | 0.2500 |

[1)]The minimum amount of serum at which the neutralizing activity becomes positive was defined as the titer of the neutralizing activity.
1 and #2 indicate the data of different rabbit individuals.

Example 7. Construction of Genes for Protein Expression in Plants

Four different types of LTB-Stx2eB combination were prepared by fusing a LTB (with or without the addition of a sugar chain) to the C terminus of a Stx2eB, and by fusing a LTB (with or without the addition of a sugar chain) to the N terminus of a Stx2eB. At this time, a Stx2eB without a sugar chain (one in which asparagine at position 73 counting from the N terminus was replaced with serine) was used as the Stx2eB, and as the LTB without a sugar chain, one in which asparagine at position 90 counting from the N terminus was replaced with serine was used. These protein antigen genes were linked via a PG12 spacer, which has been reported to increase the amount of protein accumulation (Matsui et al, Transgenic Res, 2011, 20:735-48), or via a PG12v2 similar to the PG12, and a NtADH 5'-UTR in which neighboring sequences are modified and a AtHSP terminator were used. In addition, a tobacco (*Nicotiana tabacum*)-derived β-D-glucan exohydrolase secretory signal peptide coding sequence and an endoplasmic reticulum retention signal (HDEL) were used to increase the accumulation amount of the fusion protein antigen candidate proteins.

Specifically, the construction of plasmids for expression in plants was carried out as follows.

The LTB (wild type Asn90) fragment (excluding a secretory signal peptide to periplasm, Ala22 to Asn124) was prepared as follows. Two oligonucleotides as shown below were annealed at their 3' complementary ends, and then an elongation reaction was carried out using T4 DNA polymerase (Toyobo, Fukui, Japan). In the first stage reaction, LTB-A and LTB-B, LTB-C and LTB-D, LTB-E and LTB-F, LTB-G and LTB-H, LTB-I and LTB-J were used to prepare A+B, C+D, E+F, G+H, I+J fragments, respectively. In the second stage reaction, the fragments A+B and C+D, E+F and G+H were used to prepare A+B+C+D and E+F+G+H fragments, respectively. Finally, the fragments A+B+C+D and E+F+G+H and I+J were used to prepare a full length A+B+C+D+E+F+G+H+I+J fragment. The same procedure as described above was carried out using LTB-IN90S instead of LTB-I to prepare a LTB (Asn90Ser) mutant.

LTB-A:
(SEQ ID NO: 35)
ttggatccgcccccagaccatcaccgagttgtgcagcgagtac

LTB-B:
(SEQ ID NO: 36)
cgttgatggtgtagatttgggtgttgcggtactcgctgc

LTB-C:
(SEQ ID NO: 37)
ccatcaacgacaagatcctcagctacaccgagagcatgg

LTB-D:
(SEQ ID NO: 38)
cttgaaggtgatgatcaccatctccctcttgccggccatgctc

LTB-E:
(SEQ ID NO: 39)
atcaccttcaagagcggcgagaccttccaggtcgaggtc

LTB-F:
(SEQ ID NO: 40)
cttctggctgtcgatgtgctggctgccggggacctcgacctggaa

LTB-G:
(SEQ ID NO: 41)
gacagccagaagaaggccatcgagaggatgaaggacaccctcaggatc

LTB-H:
(SEQ ID NO: 42)
gcagagcttgtcgatcttggtctcggtgaggtaggtgatcctga

LTB-I:
(SEQ ID NO: 43)
aagctctgcgtctggaacaacaagaccccc

-continued

LTB-J:
(SEQ ID NO: 44)
aaagatctgttctccatgctgatggcggcgatgctgttgggggtcttg ttgttccagacgcagagctt LTB-IN90S:
(SEQ ID NO: 45)
aagctctgcgtctggaacagcaagaccccc Each of the resulting LTB (wild type Asn90) and LTB (Asn90Ser) fragments was digested with BamHI and BglII, and then inserted into the BamHI-BglII gap of Plasmid 14 (Matsui et al., 2009, Biosci. Biotechnol, Biochem. 73, 1628-34), which had been dephosphorylated. The resulting plasmids were each treated with BglII, followed by dephosphorylation, and a phosphorylated PG12 fragment was inserted thereto. The PG12 fragment was obtained by annealing a PG12-F primer (gatcccctggttctggtcctggttctccta) (SEQ ID NO: 46) and a PG12-R primer (gatctaggagaaccaggaccagaaccaggg) (SEQ ID NO: 47), followed by phosphorylation with T4 polynucleotide kinase (PNK) (New England Biolabs, Hitchin, UK). Then, a LTB-PG12-HDEL fragment was cleaved out from each of the resulting plasmids using BamHI and SacI, and each fragment was inserted into the BamHI-SacI gap of a 2BH plasmid (Matsui et al., Transgenic Res., 2011, 20; 735-48), to prepare pRI909L+ and pRI909L− expression plasmids.

The Stx2eBN73S-PG12v2 fusion fragment was prepared as follows. PCR was carried out using a 2BH plasmid as a template, and using a mStx2eB5-A primer (aag gatccgcggcggactgcgcgaagggcaagatcgagttctcgaagtacaacgag gac (SEQ ID NO: 48), the underline indicates the BamHIsite) and a PG12v2-R primer (aa agatctaggagaaccaggaccagaaccaggtcctct (SEQ ID NO: 49), the underline indicates the BglII site) to amplify the Stx2eBN73S-PG12v2 fragment. The resulting fragment was digested with BamHI and BglII, and inserted into the BamHI-BglII gap of Plasmid 14 (Matsui et al., 2009, Biosci. Biotechnol. Biochem., 73,1628-34), which had been dephosphorylated. The Stx2eBN73S-PG2v2-HDEL fragment was cleaved out from the resulting plasmid using BamHI and SacI, and inserted into the BamHI-SacI gap of a 2BH plasmid (pRI909E− plasmid).

The construction of an expression cassette for the agent for controlling colibacillosis according to the present invention was carried out as follows. The Stx2eBAsn73Ser-PG12v2-HDEL-HSPT fragment was cleaved out from the pRI909E− plasmid using BamHI and EcoRI. The 35S promoter-NtADHmod 5'UTR-secretory signal peptide-LTB-PG12 fragment was cleaved out from the pRI909L+ or the pRI909L− plasmid using XbaI and BglII. Both fragments were ligated and inserted into the XbaI-EcoRI gap of a 2BH plasmid, to prepare pRI909L+E− (SEQ ID NO: 23) plasmid and pRI909L−E− (SEQ ID NO: 24) plasmid for expression in plants.

The LTB-PG12-HDEL-HSPT fragment was cleaved out from the pRI909L+ plasmid or the pRI909L− plasmid using BamHI and EcoRI. The 35S promoter-NtADHmod 5'UTR-secretory signal peptide-Stx2eBAsn73Ser-PG12v2 fragment was cleaved out from the pRI909E− plasmid using XbaI and BglII. Both fragments were ligated and inserted into the XbaI-EcoRI gap of a 2BH plasmid, to prepare pRI909E−L+ (SEQ ID NO: 25) plasmid and pRI909E−L− (SEQ ID NO: 26) plasmid for expression in plants (FIG. 1).

Example 8. Gene Transfer into Lettuce Using *Agrobacterium tumefaciens*

Lettuce (*Lactuca sativa* L.), cultivar: Green wave (Takii Co., Ltd.) was seeded aseptically in MS culture medium [½×mixed salts for Murashige and Skoog medium (MS salts, Wako Pure Chemical Industries, Ltd.), 1×Murashige and Skoog vitamin solution (MS vitamins, Sigma-Aldrich), 3% sucrose, 0.8% agar, pH 5.8]. Ten to 16 days after the seeding, a true leaf was collected, and a section of approximately 5 mm square was cut out. After immersing the section in a suspension of *Agrobacterium tumefaciens* (EHA105) carrying a binary plasmid (pRI909) containing the vector construct for 10 minutes, the section was placed in a co-culture medium [1×MS salts, 1×MS vitamins, 0.05 mg/l 6-benzylaminopurine (BA), 0.1 mg/l 1-naphthylacetic acid (NAA), 0.1 M acetosyringone, 3% sucrose, 0.8% agar, pH 5.8], and cultured for two days at 25° C. in the dark. After washing with sterilized water, the section was placed on a selection medium [1×MS salts, 1×MS vitamins, 0.05 mg/l BA, 0.1 mg/NAA, 0.5 g/l polyvinylpyrrolidone (PVP), 50 mg/l kanamycin (Km), 250 mg cefotaxime (Cef), 3% sucrose, 0.8% agar, pH 5.8], and cultured at 25° C. under fluorescence light (2000 to 3000 lux). Thereafter, the section was transferred to a new selection medium every three to four days (twice per week) until adventitious shoots were obtained. Redifferentiated individuals formed from the adventitious shoots were transplanted to a rooting medium [½×MS salts, 1×MS vitamins, 0.5 g/l PVP, 250 mg Cef, 3% sucrose, 0.8% agar, pH 5.8], and cultured under the same conditions. Thereafter, the redifferentiated individuals were transplanted to a new rooting medium every three to four days (twice per week). The rooted redifferentiated individuals were transplanted to a pot, and cultured under the same conditions.

Example 9. Extraction of Protein from Lettuce

The extraction of proteins was carried out in accordance with the TCA-acetone method (Shultz et al. Plant Mol Biol Rep, 2005, 23:405), using true leaves of transgenic lettuces which had been frozen with liquid nitrogen and stored at −80° C. A quantity of 100 to 200 mg of lettuce sample was crushed using Tissue Lyzer II (QIAGEN), and to the resultant, TCA-acetone (10% trichloroacetic acid, 90% acetone, 0.07% 2-mercaptoethanol) in an amount five times the amount of the sample was added. The resultant was mixed and left to stand for one hour at −20° C., and centrifuged at 16,000×g and at 4° C. for 30 minutes to remove the supernatant, thereby obtaining precipitates containing proteins. Further, in order to remove impurities, acetone/BME (100% acetone, 0.07% 2-mercaptoethanol) in an amount five times the amount of the sample was added. The resultant was mixed and centrifuged at 16,000×g and at 4° C. for 10 minutes to remove the supernatant. The above described operation to remove impurities was carried out for two more times. The resulting precipitates were dried under reduced pressure, and suspended in extraction I buffer [0.5 M sodium chloride, 5 mM imidazole, 6M urea, 20 mM tris(hydroxymethyl)aminomethane (Tris)-HCl, pH 7.9] in an amount two times the amount of the sample. The resulting suspension was centrifuged at 16,000×g and at 4° C. for 10 minutes, and the supernatant was collected, to obtain a protein solution. The concentration of the proteins was measured using Protein Assay Kit II (Bio-Rad).

Example 10. Western Analysis

The resulting protein solution was placed in a microtube in an appropriate amount, and the same amount of sample buffer (EZ Apply, manufactured by ATTO) was added thereto. The resultant was then mixed, and heated for five minutes in boiling water to carry out SDS treatment of the sample. The purified LTB+ was used as a standard reference material when carrying out the quantification of proteins. The purified LTB+ was repeatedly diluted two-fold using the extraction I buffer to prepare a serial dilution, and the serial dilution was used as a standard.

The electrophoresis (SDS-PAGE) of the proteins was carried out using an electrophoresis tank (Mini Protean Tetracell) and Mini Protean TGX-gel (BIO RAD). An electrophoresis buffer (EZ Run, manufactured by ATTO) was added, 5 μl of the SDS-treated sample was applied to a well, and the electrophoresis was carried out at a constant voltage of 200 V for 40 minutes.

After the electrophoresis, the blotting of the gel was carried out using a Trans-Blot Transfer Pack (BIO RAD) and Trans-Blot Turbo (BIO RAD).

The blotted membrane was immersed in a blocking solution (TBS-based, pH 7.2, Nakalai Tesque, Inc.), followed by shaking at room temperature for one hour, or left to stand at 4° C. for 16 hours. The membrane was then shaken in TBS-T (137 mM sodium chloride, 2.68 mM potassium chloride, 1% polyoxyethylene sorbitan monolaurate, 25 mM Tris-HCl, pH 7.4) at room temperature for five minutes, and the shaking was repeated for a total of three times to carry out washing. An anti-serum, Rabbit-Antiserum Anti-LTp 991109 (inactive) (0.1% NaN3) AO, diluted 10,000-fold with TBS-T, was used for the detection of the LTB protein. The membrane was immersed in the resulting diluted liquid, followed by shaking at room temperature for two hours to allow an antigen-antibody reaction to proceed. The membrane was then shaken in TBS-T at room temperature for five minutes, and the shaking was repeated for a total of three times to carry out washing. Anti-Rabbit IgG, AP-linked Antibody (Cell Signaling TECHNOLOGY) diluted 10,000-fold with TBS-T was used as a second antibody. The membrane was immersed in the resulting diluted liquid, followed by shaking at room temperature for one hour to allow an antigen-antibody reaction to proceed. The membrane was then shaken in TBS-T at room temperature for five minutes, and the shaking was repeated for a total of three times to carry out washing. To carry out a chromogenic reaction with alkaline phosphatase, the washed membrane was immersed in a chromogenic solution (0.1 M sodium chloride, 5 mM chlorinated magnesium, 0.33 mg/ml nitro blue tetrazolium, 0.33 mg/ml 5-bromo-4-chloro-3-indolyl-phosphoric acid, 0.1 M Tris-HCl, pH 9.5), followed by shaking at room temperature for seven minutes. The membrane was then washed with distilled water and dried at normal temperature.

The stained membrane was imaged at a resolution of 600 dpi using a scanner (PM-A900, Epson), and the quantification of the LTB protein was carried out using an image analysis software (CS Analyzer ver. 3.0, ATTO).

The results of the expression analysis of the fusion protein expressed in the transgenic lettuces prepared with the constructs shown in FIG. 1 are shown in FIG. 3. In each of the transgenic lettuces prepared with L−E− and E−L− in which a mutation was introduced into the N-linked glycosylation site, one band was detected at a position corresponding to the estimated molecular weight (about 20 kDa) (FIG. 3A). In each of the transgenic lettuces prepared with L+E− and E−L+, a band at a higher molecular weight was also observed, in addition to the band at 20 kDa, by which the addition of an N-linked sugar chain can be assumed. The amounts of the fusion protein antigens accumulated in respective transgenic lettuces are shown in FIG. 3B. It can be seen from the figure that the accumulation of the fusion protein antigen tends to be higher in the transgenic lettuces prepared with the LTB (L+) with an N-linked sugar chain as compared to those prepared with the LTB (L−) without an N-linked sugar chain, and that the arrangement order in which the Stx2eB is disposed on the N terminus side tends to result in a higher accumulation.

Example 11. Confirmation of Antigenicity (Antibody Induction) of Recombinant Protein To confirm the antigenicity (antibody induction) of: the B subunit of *Escherichia coli* heat-labile toxin (L+); the LTB glycosylation site mutant (L−); and the fusion protein (L+E−) of L+ and the glycosylation site mutant of the B subunit of edema disease toxin (Stx2eB); each of the purified proteins was emulsified with a complete (or incomplete) Freund's adjuvant, and used to immunize rabbits by subcutaneous administration. Each of the emulsions was administered in an amount of 50 μg at the first time, and administered four more times (100 μg per administration) at intervals of two weeks to boost the immunization. After confirming by ELISA that the antibody titer against the antigen was sufficiently increased, whole blood was collected from each of the rabbits, and serum was separated by centrifugation.

Example 12. Oral Immunization of Mice with Transgenic Lettuce

Six week-old Balb/c male mice were introduced and habituated. The collection of blood was carried out before the immunization, and the immunization was started at 8 week-old. A powder of each of the transgenic lettuces containing LTB in an amount corresponding to about 90 μg was suspended in saline, and the resulting suspension was orally administered to mice using a stomach tube. The doses of the respective lettuce powders were adjusted such that an equal amount of LTB was contained in each of the doses. The oral administration was carried out every seven days, for a total of four times. On day 10 and day 28 after the first administration, the blood was collected, and serum was separated. The serum was inactivated by treating at 56° C. for 30 minutes. The oral administration of the powder of the transgenic lettuce was carried out in the same manner, such that the transgenic lettuce powder containing LTB in an amount corresponding to 65 μg was administered. The collection of blood was carried out periodically, and serum was separated and inactivated. The collection of intestinal lavage solution was carried out by cutting out the entire length of the large intestine, and 5 cm of small intestine from its ileocecum, and then by washing them with 5 ml of PBS. The resultants were stored until use at −80° C., and a protease inhibitor was added thereto when measuring the antibody titter.

Example 13. Oral Immunization of Rabbits with Transgenic Lettuce

Japanese white rabbits each having a body weight of 2.5 kg were introduced and habituated, and the collection of blood was carried out before the immunization. A powder of each of the transgenic lettuces containing LTB in an amount corresponding to 2 mg was suspended in saline, and the resulting suspension was orally administered to rabbits every seven days for a total of six times. The dosages of L+E− and L+ per administration were adjusted such that 2 mg equivalent of LTB (L+E−: 0.85 g of lettuce powder; L+: 1.5 g of lettuce powder) was contained in each of the doses. The dosage of lettuce prepared with empty vector, which was the negative control, was 1.0 g lettuce powder per administration. On day 10, day 28, and day 44 after the first administration, blood was collected from each of the rabbits, and serum was separated. The serum was inactivated by treating at 56° C. for 30 minutes. IgG was purified using a protein G column, and used for the measurement of the neutralizing activity.

Example 14. Measurement of Toxin Neutralizing Activity Against Stx2e

The measurement of the neutralizing activity of an anti-Stx2e toxin antibody in the serum was carried out by Vero cell assay. Into a 96-well cell culture plate, $1\times10^4$/well of Vero cells (cultured cells derived from the renal epithelium of African green monkey) were seeded. After culturing the cells for two days, Stx2e in an amount of four times the 50% lethal dose of the cells was added to the plate, and the resultant was incubated for three days in a carbon dioxide incubator (5% $CO_2$, 37° C.). The determination of life and death of the Vero cells were carried out by measuring the activity of intracellular dehydrogenases using a Cell Counting Kit (DOJINDO).

Example 15. Measurement of Toxin Neutralizing Activity Against Swine Diarrheagenic Heat-Labile Enterotoxin (LTp)

The measurement of the neutralizing activity of an anti-LTp toxin antibody in the serum was carried out by CHO cell assay. To a 8-well chamber slide, the serum to be tested, and LTp in an amount to achieve a final concentration of 20 ng/mL, were added, and $2.5\times10^3$/well of CHO cells (Chinese hamster ovary cells) were seeded on the plate, followed by culturing in a carbon dioxide incubator (5% $CO_2$, 37° C.) for 24 hours. After the culture, the shapes of the CHO cells were observed, and cells whose longer diameter was longer than twice the length of the shorter diameter were defined as atypical cells. The ratio of the atypical cells with respect to the total number of cells was calculated, and those in which the ratio of the calculated atypical cell-ratio to the ratio of spontaneously-occurring atypical cell-ratio was equal to or less than 50% were defined to have a positive neutralizing activity. The minimum amount of serum at which the neutralizing activity becomes positive was defined as the titer of the neutralizing activity.

Example 16. Measurement of Antibody Titer

The measurement of the antibody titer was carried out using an ELISA plate in which 2.5 g/mL of antigen was immobilized at 100 μL/well (Maxisorp, Nunc). As antigens, a detoxified Stx2e which had been purified was used for the measurement of the anti-Stx2e antibody titer, and a purified LTp was used for the measurement of the anti-LTp antibody titer. A two-fold serial dilution of the serum to be tested was prepared with a diluent containing 0.1% (w/v) bovine serum albumin, and applied to the ELISA plate. A horseradish peroxidase (HRP)-labeled antibody was used as a secondary antibody, and detection was carried out by a chromogenic method using hydrogen peroxide as a substrate and ABTS (2,2'-azino-bis(3-ethylbenzothiazoline-6-sulphonic acid)) as a chromogenic agent. An absorbance value equal to or more than twice the value of the average absorbance of the diluent which was a negative control was defined as the positive antibody titer, and the value of the maximum dilution ratio at which the antibody titer becomes positive was defined as the antibody titer of the serum. If antibody titer was detected in the serum before the immunization, a value obtained by subtracting the value of the antibody titer detected before the immunization was defined as the antibody titer of the serum. The results are shown in FIGS. 4 to 7.

Increases in both serum IgG and IgA antibody titers (FIGS. 4 and 5), and an increase in IgA antibody titer in the intestinal lavage solution (FIG. 6) were observed in the mice administered with protein antigen-producing lettuces. These results confirmed that it is possible to induce the anti-LTp antibody by the oral administration of a fusion protein antigen-producing plant. No marked difference in the ability to induce antibodies was observed between the respective lettuces prepared with different types of constructs.

Figure 7:
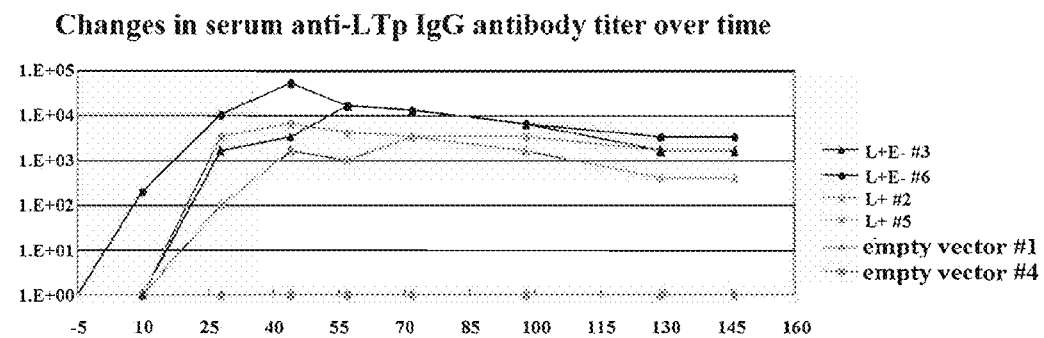
FIG. 7 is a graph illustrating the changes in the anti-IgG antibody titer over time, in the serum of rabbits orally administered with the transformed plants.

In the groups administered with the protein antigen-producing lettuces, an increase in the anti-LTp antibody titer was confirmed (FIG. 7). IgG was purified from the serum collected on day 44 when the antibody titer was sufficiently increased, and the evaluation of the neutralizing activity against LTp toxin was carried out. The neutralizing activity was confirmed in both the two rabbits immunized with L+E−, and one of the two rabbits immunized with L+ (Table 2).

TABLE 2

Results of IgG analysis of rabbit serum collected on day 44 after the administration of lettuce

| Construct | Administration route | Rabitt ID | Anti-LT antibody titer | Neutralizing activity against LT toxin |
|---|---|---|---|---|
| Negative control lettuce | Oral administration (transgenic lettuce) | 1 | 1 | − |
| | | 4 | 1 | − |
| L + lettuce | | 2 | 1600 | ? |
| | | 5 | 6400 | + |
| L + L-lettuce | | 3 | 25600 | + |
| | | 6 | 25600 | + |

Example 17. Edema Disease Bacteria Challenge Test

Figure 8:
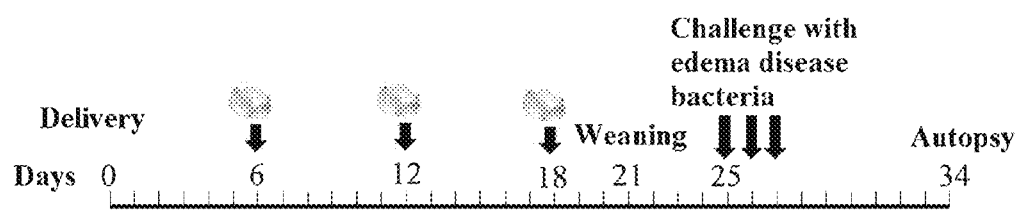
FIG. 8 illustrates the effect of oral administration of the transformed plants on the prevention of edema disease of swine.
Figure 8:
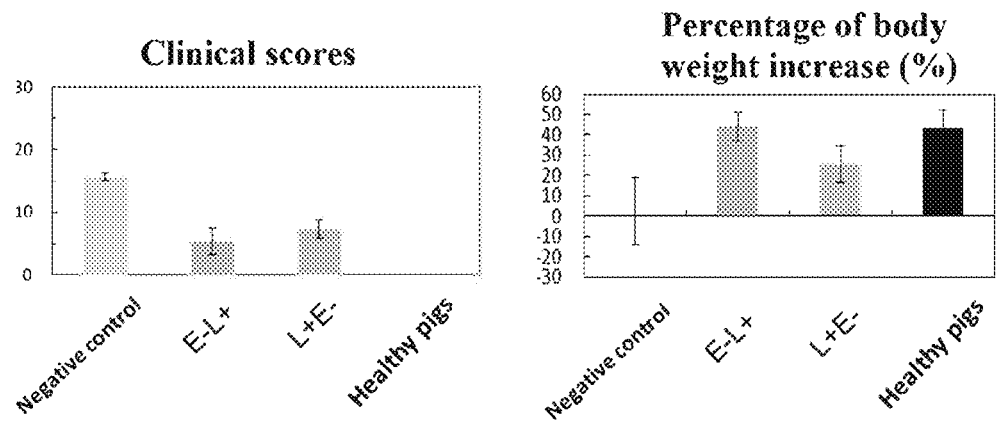

A test for confirming the effect of preventing the edema disease was carried out by oral administration of the protein antigen-producing lettuces. The young pigs selected for the test were fed with artificial milk without feeding colostrum until 24 hours after the delivery, and returned to be breastfed by mother pigs thereafter. Three pigs were selected for each of the test groups. On days 6, 12 and 18 after the delivery, a solution obtained by suspending the freeze-dried powder of each of the protein antigen-producing lettuces (each containing Stx2eB in an amount corresponding to 2.3 mg) or of the lettuce prepared with empty vector in water was administered by forced feeding using a syringe connected to a tube. Shiga toxin-producing *Escherichia coli* derived from pig (STEC, Obihiro-strain, ST-, LT-) filled in enteric capsules was administered to pigs on days 25, 26 and 27, to carry out the challenge test. The body weight and the amount of feed intake of the pigs were measured. Further, their clinical manifestations were observed every day, and the following typical symptoms associated with edema disease of swine were observed and scored based on the following standards: stamina (0: normal, 1: reduced, 2: lost), edema around the eyes (0: no, 1: mild, 2: moderate, 3: severe), and neurological symptoms (0: no, 1: mild, 2: moderate, 3: severe). Further, the collection of blood and the collection of stool were carried out periodically, and the titer of the antibody specific to Stx2eB was measured by ELISA. The pigs were euthanized on day 7 after the challenge with STEC, subjected to an autopsy, and the abnormalities in each of their organs and tissue were macroscopically observed. Pathology specimens of primary organs were prepared, and histopathological findings were examined. The results are shown in FIG. 8.

The effect of preventing edema disease was observed in both of the groups administered with E−L+ and with L+E−, in both the indices of clinical manifestation and body weight.

INDUSTRIAL APPLICABILITY

The agent for controlling *Escherichia coli* diarrhea according to the present invention is useful in the field of livestock farming.

The invention claimed is:

1. A method for controlling diarrhea comprising administering an effective amount of a fusion protein comprising a subunit of Shiga toxin and a subunit of *Escherichia coli* heat-labile toxin to an animal in need thereof,
wherein:
the subunit of Shiga toxin and the subunit of *Escherichia coli* heat-labile toxin each is a B subunit,
an N-linked sugar chain has been added to the Asn residue corresponding to position 90 of the amino acid sequence of SEQ ID NO: 12 of the B subunit of *Escherichia coli* heat-labile toxin, and
the subunit of *Escherichia coli* heat-labile toxin has been fused to the N terminus side of the subunit of Shiga toxin.

2. The method according to claim 1, wherein the subunit of Shiga toxin and the subunit of *Escherichia coli* heat-labile toxin have been fused via a peptide linker.

3. The method according to claim 1, wherein the Asn residue corresponding to position 55 of the amino acid sequence of SEQ ID NO: 8 of the B subunit of the Shiga toxin has been replaced by Ser.

4. The method according to claim 1, wherein the fusion protein induces antibodies against the *Escherichia coli* heat-labile toxin.

5. The method according to claim 4, wherein the fusion protein induces IgA.

6. The method according to claim 4, wherein the fusion protein induces IgG.

7. The method according to claim 1, wherein:
the subunit of Shiga toxin and the subunit of *Escherichia coli* heat-labile toxin have been fused via a peptide linker, and
the Asn residue corresponding to position 55 of the amino acid sequence of SEQ ID NO: 8 of the B subunit of the Shiga toxin has been replaced by Ser.

8. A method for controlling diarrhea in a non-human animal, the method comprising administering an effective amount of an edible plant transformed with a recombinant vector comprising a DNA construct containing a DNA which codes for a fusion protein comprising a subunit of Shiga toxin and a subunit of *Escherichia coli* heat-labile toxin to the non-human animal in need thereof,
wherein:
the subunit of Shiga toxin and the subunit of *Escherichia coli* heat-labile toxin each is a B subunit,
an N-linked sugar chain has been added to the Asn residue corresponding to position 90 of the amino acid sequence of SEQ ID NO: 12 of the B subunit of *Escherichia coli* heat-labile toxin, and
the subunit of *Escherichia coli* heat-labile toxin has been fused to the N terminus side of the subunit of Shiga toxin.

9. The method according to claim 8, wherein the subunit of Shiga toxin and the subunit of *Escherichia coli* heat-labile toxin have been fused via a peptide linker.

10. The method according to claim 8, wherein the Asn residue corresponding to position 55 of the amino acid sequence of SEQ ID NO: 8 of the B subunit of the Shiga toxin has been replaced by Ser.

11. The method according to claim 8, wherein:
the subunit of Shiga toxin and the subunit of *Escherichia coli* heat-labile toxin have been fused via a peptide linker, and the Asn residue corresponding to position 55 of the amino acid sequence of SEQ ID NO: 8 of the B subunit of the Shiga toxin has been replaced by Ser.

* * * * *